US007150969B2

(12) United States Patent
Kan et al.

(10) Patent No.: US 7,150,969 B2
(45) Date of Patent: Dec. 19, 2006

(54) ALTERNATIVELY SPLICED ISOFORM OF ACETYL-COA CARBOXYLASE 2 (ACC2)

(75) Inventors: Zhengyan Kan, Bellevue, WA (US); Philip W. Garrett-Engele, Seattle, WA (US); Christopher D. Armour, Kirkland, WA (US); Christopher K. Raymond, Seattle, WA (US); John C. Castle, Seattle, WA (US)

(73) Assignee: Rosetta Inpharmatics LLC, Seattle, WA (US)

( * ) Notice: Subject to any disclaimer, the term of this patent is extended or adjusted under 35 U.S.C. 154(b) by 0 days.

(21) Appl. No.: 11/144,368

(22) Filed: Jun. 3, 2005

(65) Prior Publication Data

US 2005/0272082 A1    Dec. 8, 2005

Related U.S. Application Data

(60) Provisional application No. 60/577,234, filed on Jun. 4, 2004.

(51) Int. Cl.
| | |
|---|---|
| C12Q 1/48 | (2006.01) |
| C12Q 1/68 | (2006.01) |
| C12N 15/70 | (2006.01) |
| C12N 9/10 | (2006.01) |
| C12N 5/16 | (2006.01) |
| C07H 21/04 | (2006.01) |

(52) U.S. Cl. ............... 435/6; 435/4; 435/183; 435/320.1; 435/69.2; 536/23.2

(58) Field of Classification Search ............... 435/183, 435/23.2, 6
See application file for complete search history.

(56) References Cited

U.S. PATENT DOCUMENTS

| | | | |
|---|---|---|---|
| 5,480,784 A | 1/1996 | Kacian et al. | |
| 5,616,459 A | 4/1997 | Kramer et al. | |
| 5,849,902 A | 12/1998 | Arrow et al. | |
| 5,852,188 A | 12/1998 | Cook | |
| 5,859,221 A | 1/1999 | Cook et al. | |
| 6,324,479 B1 | 11/2001 | Friend et al. | |
| 6,485,941 B1 | 11/2002 | Waldrop et al. | |
| 6,518,035 B1 | 2/2003 | Ashby et al. | |
| 2003/0144345 A1 | 7/2003 | Gubler et al. | |
| 2003/0187254 A1 | 10/2003 | Perry et al. | |

FOREIGN PATENT DOCUMENTS

| | | |
|---|---|---|
| WO | WO 02/079501 | 10/2002 |
| WO | WO 04/013159 | 2/2004 |
| WO | WO 06/004549 | 1/2006 |

OTHER PUBLICATIONS

Abe K;Shinohara Y;Terada H; "Isolation and characterization of cDNA encoding rat heart type acetyl-CoA carboxylase" 1998, Biochim Biophys Acta 1398(3):347-352.
Abu-Elheiga L;Almarza-Ortega DB;Baldini A;Wakil SJ; "Human acetyl-CoA carboxylase 2. Molecular cloning, characterization, chromosomal mapping, and evidence for two isoforms" 1997, J Biol Chem 272(16):10669-10677.
Abu-Elheiga L;Brinkley WR;Zhong L;Chirala SS;Woldegiorgis G;Wakil SJ; "The subcellular localization of acetyl-CoA carboxylase 2" 2000, Proc Natl Acad Sci U S A 97(4):1444-1449.
Abu-Elheiga L;Jayakumar A;Baldini A;Chirala SS;Wakil SJ; "Human acetyl-CoA carboxylase: characterization, molecular cloning, and evidence for two isoforms" 1995, Proc Natl Acad Sci U S A 92(9):4011-4015.
Abu-Elheiga L;Matzuk MM;Abo-Hashema KA;Wakil SJ; "Continuous fatty acid oxidation and reduced fat storage in mice lacking acetyl-CoA carboxylase 2" 2001, Science 291(5513):2613-2616.
Abu-Elheiga L;Oh W;Kordari P;Wakil SJ; "Acetyl-CoA carboxylase 2 mutant mice are protected against obesity and diabetes induced by high-fat/high-carbohydrate diets" 2003, Proc Natl Acad Sci U S A 100(18):10207-10212.
Barber MC;Price NT;Travers MT; "Structure and regulation of acetyl-CoA carboxylase genes of metazoa" 2005, Biochim Biophys Acta 1733(1):1-28.
Bernstein E;Caudy AA;Hammond SM;Hannon GJ; "Role for a bidentate ribonuclease in the initiation step of RNA interference" 2001, Nature 409(6818):363-366.
Bianchi A;Evans JL:Iverson AJ;Nordlund AC;Watts TD;Witters LA; "Identification of an isozymic form of acetyl-CoA carboxylase" 1990, J Biol Chem 265(3):1502-1509.
Cramer CT;Goetz B;Hopson KL;Fici GJ;Ackermann RM;Brown SC;Bisgaier CL;Rajeswaran WG;Oniciu DC;Pape ME; "Effects of a novel dual lipid synthesis inhibitor and its potential utility in treating dyslipidemia and metabolic syndrome" 2004, J Lipid Res 45(7):1289-1301.
Davies SP;Sim AT;Hardie DG; "Location and function of three sites phosphorylated on rat acetyl-CoA carboxylase by the AMP-activated protein kinase" 1990, Eur J Biochem 187(1):183-190.

(Continued)

*Primary Examiner*—Rebecca E. Prouty
*Assistant Examiner*—Iqbal Chowdhury
(74) *Attorney, Agent, or Firm*—R. Douglas Bradley

(57) ABSTRACT

The present invention features nucleic acids and polypeptides encoding novel splice variant isoforms of acetyl-CoA carboxylase 2 (ACC2). The polynucleotide sequence of ACC2sv1 is provided by SEQ ID NO 3. The amino acid sequence of ACC2sv1 is provided by SEQ ID NO 4. The present invention also provides methods for using ACC2sv1 polynucleotides and proteins to screen for compounds that bind to ACC2sv1.

9 Claims, 1 Drawing Sheet

OTHER PUBLICATIONS den Boer ME;Dionisi-Vici C;Chakrapani A;van Thuijl AO; Wanders RJ;Wijburg FA; "Mitochondrial trifunctional protein deficiency; a severe fatty acid oxidation disorder with cardiac and neurologic involvement" 2003, J Pediatr 142(6):684-689.

Dyck JR;Lopaschuk GD; "Malonyl CoA control of fatty acid oxidation in the ischemic heart" 2002, J Mol Cell Cardiol 34(9):1099-1109.

Elbashir SM;Harborth J;Lendeckel W; Yalcin A; Weber K;Tuschl T; "Duplexes of 21-nucleotide RNAs mediate RNA interference in cultured mammalian cells" 2001, Nature 411(6836):494-498.

Fire A;Xu S;Montgomery MK;Kostas SA;Driver SE;Mello CC; "Potent and specific genetic interference by double-stranded RNA in Caenorhabditis elegans" 1998, Nature 391 (6669):806-811.

Florea L;Hartzell G;Zhang Z;Rubin GM;Miller W; "A computer program for aligning a cDNA sequence with a genomic DNA sequence" 1998, Genome Res 8(9):967-974.

Gregersen N;Bross P;Andresen BS; "Genetic defects in fatty acid beta-oxidation and acyl-CoA dehydrogenases. Molecular pathogenesis and genotype-phenotype relationships" 2004, Eur J Biochem 271(3):470-482.

Guertl B;Noehammer C;Hoefler G; "Metabolic cardiomyopathies" 2000, Int J Exp Pathol 81(6);349-372.

Ha J;Lee JK;Kim KS;Witters LA;Kim KH; "Cloning of human acetyl-CoA carboxylase-beta and its unique features" 1996, Proc Natl Acad Sci U S A 93(21):11466-11470.

Hamilton AJ;Baulcombe DC; "A species of small antisense RNA in posttranscriptional gene silencing in plants" 1999, Science 286(5441):950-952.

Hammond SM;Boettcher S;Caudy AA;Kobayashi R;Hannon GJ; "Argonaute2, a link between genetic and biochemical analyses of RNAi" 2001, Science 293(5532):1146-1150.

Hardie DG; Hawley SA; "AMP-activated protein kinase: the energy charge hypothesis revisited" 2001, Bioessays 23(12):1112-1119.

Harwood HJ;Petras SF;Shelly LD;Zaccaro LM;Perry DA;Makowski MR;Hargrove DM;Martin KA;Tracey WR;Chapman JG;Magee WP;Dalvie DK:Soliman VF;Martin WH;Mularski CJ;Eisenbeis SA; "Isozyme-nonselective N-substituted bipiperidylcarboxamide acetyl-CoA carboxylase inhibitors reduce tissue malonyl-CoA concentrations, inhibit fatty acid synthesis, and increase fatty acid oxidation in cultured cells and in experimental animals" 2003, J Biol Chem 278(39):37099-37111.

Kafert S;Krauter J;Ganser A;Eder M; "Differential quantitation of alternatively spliced messenger RNAs using isoform-specific real-time RT-PCR" 1999, Anal Biochem 269(1):210-213.

Kan Z;Rouchka EC;Gish WR;States DJ; "Gene structure prediction and alternative splicing analysis using genomically aligned ESTs" 2001, Genome Res 11(5):889-900.

Kan Z;States D;Gish W; "Selecting for functional alternative splices in ESTs" 2002, Genome Res 12(12):1837-1845.

Kennerdell JR;Carthew RW; "Use of dsRNA-mediated genetic interference to demonstrate that frizzled and frizzled 2 act in the wingless pathway" 1998, Cell 95(7):1017-1026.

Kim KH; "Regulation of mammalian acetyl-coenzyme A carboxylase" 1997, Annu Rev Nutr 17(0):77-99.

Kohler G;Milstein C; "Continuous cultures of fused cells secreting antibody of predefined specificity" 1975, Nature 256(5517):495-497.

Kudo N;Barr AJ;Barr RL;Desai S;Lopaschuk GD; "High rates of fatty acid oxidation during reperfusion of ischemic hearts are associated with a decrease in malonyl-CoA levels due to an increase in 5'-AMP-activated protein kinase inhibition of acetyl-CoA carboxylase" 1995, J Biol Chem 270(29):17513-17520.

Lee JJ;Moon YA;Ha JH;Yoon DJ;Ahn YH;Kim KS; "Cloning of human acetyl-CoA carboxylase beta promoter and its regulation by muscle regulatory factors" 2001, J Biol Chem 276(4):2576-2585.

Minokoshi Y;Kim YB;Peroni OD;Fryer LG;Muller C;Carling D;Kahn BB; "Leptin stimulates fatty-acid oxidation by activating AMP-activated protein kinase" 2002, Nature 415(6869);339-343.

Mironov AA;Fickett JW;Gelfand MS; "Frequent alternative splicing of human genes" 1999, Genome Res 9(12):1288-1293.

Misquitta L;Paterson BM; "Targeted disruption of gene function in Drosophila by RNA interference (RNA-i): a role for nautilus in embryonic somatic muscle formation" 1999, Proc Natl Acad Sci U S A 96(4):1451-1456.

Modrek B;Resch A;Grasso C;Lee C; "Genome-wide detection of alternative splicing in expressed sequences of human genes" 2001, Nucleic Acids Res 29(13):2850-2859.

Moller DE; "New drug targets for type 2 diabetes and the metabolic syndrome" 2001, Nature 414(6865):821-827.

Munday MR;Hemingway CJ; "The regulation of acetyl-CoA carboxylase—a potential target for the action of hypolipidemic agents" 1999, Adv Enzyme Regul 39(0):205-234.

Oh SY;Park SK;Kim JW; Ahn YH;Park SW;Kim KS; "Acetyl-CoA carboxylase beta gene is regulated by sterol regulatory element-binding protein-1 in liver" 2003, J Biol Chem 278(31):28410-28417.

Olpin SE; "Implications of Impaired ketogenesis in fatty acid oxidation disorders" 2004, Prostaglandins Leukot Essent Fatty Acids 70(3):293-308.

Rasmussen BB:Wolfe RR: "Regulation of fatty acid oxidation in skeletal muscle" 1999, Annu Rev Nutr 19(0):463-484.

Ruderman N;Prentki M; "AMP kinase and malonyl-CoA: targets for therapy of the metabolic syndrome" 2004, Nat Rev Drug Discov 3(4):340-351.

Ruderman NB;Saha AK;Vavvas D;Witters LA; "Malonyl-CoA, fuel sensing, and insulin resistance" 1999, Am J Physiol 276(0):0-0.

Saha AK;Laybutt DR;Dean D;Vavvas D;Sebokova E;Ellis B;Klimes I;Kraegen EW;Shafrir E;Ruderman NB; "Cytosolic citrate and malonyl-CoA regulation in rat muscle in vivo" 1999, Am J Physiol 276(0):0-0.

Sim KG;Hammond J;Wilcken B; "Strategies for the diagnosis of mitochondrial fatty acid beta-oxidation disorders" 2002, Clin Chim Acta 323(38719):37-58.

Tabara H;Sarkissian M;Kelly WG;Fleenor J;Grishok A;Timmons L;Fire A;Mello CC; "The rde-1 gene, RNA interference, and transposon silencing in C. elegans" 1999, Cell 99(2):123-132.

Taveau M;Stockholm D;Spencer M;Richard I; "Quantification of splice variants using molecular beacon or scorpion primers" 2002, Anal Biochem 305(2):227-235.

Trumble GE;Smith MA;Winder WW; "Purification and characterization of rat skeletal muscle acetyl-CoA carboxylase" 1995, Eur J Biochem 231(1):192-198.

Ullrich CK; Widmer J;Park JP;Mohandas TK;Witters LA; "Assignment of acetyl-CoA carboxylase-beta (ACACB) to human chromosome band 12q24.1 by in situ hybridization" 1997, Cytogenet Cell Genet 77(38780):176-177.

Vandenbroucke II; Vandesompele J;Paepe AD;Messiaen L; "Quantification of splice variants using real-time PCR" 2001, Nucleic Acids Res 29(13):0-0.

Vavvas D;Apazidis A;Saha AK; Gamble J;Patel A;Kemp BE;Witters LA;Ruderman NB; "Contraction-induced changes in acetyl-CoA carboxylase and 5'-AMP-activated kinase in skeletal muscle" 1997, J Biol Chem 272(20):13255-13261.

Widmer J;Fassihi KS; Schlichter SC; Wheeler KS;Crute BE;King N;Nutile-McMenemy N;Noll WW;Daniel S;Ha J;Kim KH; Witters LA; "Identification of a second human acetyl-CoA carboxylase gene" 1996, Biochem J 0(0):915-922.

Winder WW;Wilson HA;Hardie DG;Rasmussen BB;Hutber CA;Call GB;Clayton RD;Conley LM;Yoon S;Zhou B; "Phosphorylation of rat muscle acetyl-CoA carboxylase by AMP-activated protein kinase and protein kinase A" 1997, J Appl Physiol 82(1):219-225.

Witters LA;Watts TD;Daniels DL;Evans JL; "Insulin stimulates the dephosphorylation and activation of acetyl-CoA carboxylase" 1988, Proc Natl Acad Sci U S A 85(15):5473-5477.

Zhang H;Tweel B;Tong L; "Molecular basis for the inhibition of the carboxyltransferase domain of acetyl-coenzyme-A carboxylase by haloxyfop and diclofop" 2004, Proc Natl Acad Sci U S A 101(16):5910-1915.

SEQUENCE LISTING

<160> NUMBER OF SEQ ID NOS: 26

<210> SEQ ID NO 1
<211> LENGTH: 40
<212> TYPE: DNA
<213> ORGANISM: Homo sapiens

<400> SEQUENCE: 1
ttccctgatc gcgaagtaaa gccgagcatg tcgggactcc                                40

<210> SEQ ID NO 2
<211> LENGTH: 261
<212> TYPE: DNA
<213> ORGANISM: Homo sapiens

<400> SEQUENCE: 2
catttcggga tggagcaagc gcagcgcgaa gttgggcgcc cgccggctgc agcagaaccc        60
cgcccgcggc gctctaggac tgcatctcgg cctccgggtc gcgacctggc tgtcctgctg       120 ggtcccggc ctcgggtcgg cttcaggcgg ttaagggggtg catgctctgc accctgcgg        180 gagcccggtg ggattggcct gcggggtggt caacatgagt cctgccaagt gcaagatctg       240
tttccctgat cgcgaagtaa a                                                  261

<210> SEQ ID NO 3
<211> LENGTH: 6768
<212> TYPE: DNA

<213> ORGANISM: Homo sapiens

<400> SEQUENCE: 3

| | | | | | |
|---|---|---|---|---|---|
| atgagtcctg | ccaagtgcaa | gatctgtttc | cctgatcgcg | aagtaaagcc | gagcatgtcg | 60 |
| ggactccacc | tggtgaagag | gggacgggaa | cacaagaagc | tggacctgca | cagagacttt | 120 |
| accgtggctt | ctcccgctga | gtttgtcaca | cgctttgggg | gggatcgggt | catcgagaag | 180 |
| gtgcttattg | ccaacaacgg | gattgccgcc | gtgaagtgca | tgcgctccat | ccgcaggtgg | 240 |
| gcctatgaga | tgttccgcaa | cgagcgggcc | atccggtttg | ttgtgatggt | gaccccgag | 300 |
| gaccttaagg | ccaacgcaga | gtacatcaag | atggcggatc | attacgtccc | cgtcccagga | 360 |
| gggcccaata | caacaacta | tgccaacgtg | gagctgattg | tggacattgc | caagagaatc | 420 |
| cccgtgcagg | cggtgtgggc | tggctgggc | catgcttcag | aaaaccctaa | acttccggag | 480 |
| ctgctgtgca | agaatggagt | tgctttctta | ggccctccca | gtgaggccat | gtgggcctta | 540 |
| ggagataaga | tcgcctccac | cgttgtcgcc | cagacgctac | aggtcccaac | cctgccctgg | 600 |
| agtggaagcg | gcctgacagt | ggagtggaca | aagatgatc | tgcagcaggg | aaaaagaatc | 660 |
| agtgtcccag | aagatgttta | tgacaagggt | tgcgtgaaag | acgtagatga | gggcttggag | 720 |
| gcagcagaaa | gaattggttt | tccattgatg | atcaaagctt | ctgaaggtgg | cggagggaag | 780 |
| ggaatccgga | aggctgagag | tgcggaggac | ttcccgatcc | ttttcagaca | agtacagagt | 840 |
| gagatcccag | gctcgcccat | ctttctcatg | aagctggccc | agcacgcccg | tcacctggaa | 900 |
| gttcagatcc | tcgctgacca | gtatgggaat | gctgtgtctc | tgtttggtcg | cgactgctcc | 960 |
| atccagcggc | ggcatcagaa | gatcgttgag | gaagcaccgg | ccaccatcgc | ccgctggcc | 1020 |
| atattcgagt | tcatggagca | gtgtgccatc | cgcctggcca | agaccgtggg | ctatgtgagt | 1080 |
| gcagggacag | tggaataacct | ctatagtcag | gatggcagct | tccacttctt | ggagctgaat | 1140 |
| cctcgcttgc | aggtggaaca | tccctgcaca | gaaatgattg | ctgacgttaa | tctgccggcc | 1200 |
| gcccagctac | agatcgccat | gggcgtgcca | ctgcaccggc | tgaaggatat | ccggcttctg | 1260 |
| tatgagagt | caccatgggg | agtgactccc | atttcttttg | aaacccccctc | aaaccctccc | 1320 |
| ctcgcccgag | gccacgtcat | tgctgccaga | atcaccagcg | aaaacccaga | cgagggtttt | 1380 |
| aagccgagct | ccgggactgt | ccaggaactg | aatttccgga | gcagcaagaa | cgtgtgggt | 1440 |
| tacttcagcg | tggccgctac | tggaggcctg | cacgagtttg | cggattccca | atttgggcac | 1500 |
| tgcttctcct | ggggagagaa | ccggaagag | gccatttcga | acatggtggt | ggctttgaag | 1560 |
| gaactgtcca | tccgaggtga | ctttaggact | accgtggaat | acctcattaa | cctcctggag | 1620 |
| accgagagct | tccagaacaa | cgacatcgac | accgggtggt | tggactacct | cattgctgag | 1680 |
| aaagtgcagg | cggagaaacc | ggatatcatg | cttggggtgg | tatgcgggc | cttgaacgtg | 1740 |
| gccgatgcga | tgttcagaac | gtgcatgaca | gatttcttac | actccctgga | aagggccag | 1800 |
| gtcctcccag | cggattcact | actgaacctc | gtagatgtga | aattaattta | cggaggtgtt | 1860 |
| aagtacattc | tcaaggtggc | ccggcagtct | ctgaccatgt | tcgttctcat | catgaatggc | 1920 |
| tgccacatcg | agattgatgc | ccaccggctg | aatgatgggg | ggctcctgct | ctcctacaat | 1980 |
| gggaacagct | acaccaccta | catgaaggaa | gaggttgaca | gttaccgaat | taccatcggc | 2040 |
| aataagacgt | gtgtgtttga | aaggagaac | gatcctacag | tcctgagatc | ccctcggct | 2100 |
| gggaagctga | cacagtacac | agtggaggat | gggggccacg | ttgaggctgg | gagcagctac | 2160 |
| gctgagatgg | aggtgatgaa | gatgatcatg | accctgaacg | ttcaggaaag | aggccgggtg | 2220 |
| aagtacatca | gcgtccagg | tgccgtgctg | gaagcaggct | gcgtggtggc | caggctggag | 2280 |

```
ctcgatgacc cttctaaagt ccacccggct gaaccgttca caggagaact ccctgcccag  2340
cagacactgc ccatcctcgg agagaaactg caccaggtct tccacagcgt cctggaaaac  2400
ctcaccaacg tcatgagtgg cttttgtctg ccagagcccg ttttagcat aaagctgaag   2460 gagtgggtgc agaagctcat gatgaccctc cggcacccgt cactgccgct gctggagctg  2520
caggagatca tgaccagcgt ggcaggccgc atccccgccc ctgtggagaa gtctgtccgc  2580
agggtgatgg cccagtatgc cagcaacatc acctcggtgc tgtgccagtt ccccagccag  2640
cagatagcca ccatcctgga ctgccatgca gccaccctgc agcggaaggc tgatcgagag  2700
gtcttcttca tcaacaccca gagcatcgtg cagttggtcc agagataccg cagcgggatc  2760
cgcggctata tgaaaacagt ggtgttggat tccctgagaa gatacttgcg tgttgagcac  2820 catttcagc aagcccacta cgacaagtgt gtgataaacc tcaggagca gttcaagcca   2880 gacatgtccc aggtgctgga ctgcatcttc tcccacgcac aggtggccaa gaagaaccag  2940
ctggtgatca tgttgatcga tgagctgtgt ggcccagacc cttccctgtc ggacgagctg  3000
atctccatcc tcaacgagct cactcagctg agcaaaagcg agcactgcaa agtggccctc  3060
agagcccggc agatcctgat tgcctcccac ctcccctcct acgagctgcg gcataaccag  3120
gtggagtcca ttttcctgtc tgccattgac atgtacggcc accagttctg ccccgagaac  3180
ctcaagaaat taatactttc ggaaacaacc atcttcgacg tcctgcctac tttcttctat  3240
cacgcaaaca aagtcgtgtg catggcgtcc ttggaggttt acgtgcggag gggctacatc  3300
gcctatgagt taaacagcct gcagcaccgg cagctcccgg acggcacctg cgtggtagaa  3360
ttccagttca tgctgccgtc ctcccaccca aaccggatga ccgtgcccat cagcatcacc  3420
aaccctgacc tgctgaggca cagcacagag ctcttcatgg acagcggctt ctccccactg  3480
tgccagcgca tgggagccat ggtagccttc aggagattcg aggacttcac cagaaatttt  3540
gatgaagtca tctcttgctt cgccaacgtg cccaaagaca ccccctctt cagcgaggcc   3600 cgcacctccc tatactccga ggatgactgc aagagcctca gagaagagcc catccacatt  3660
ctgaatgtgt ccatccagtg tgcagaccac ctggaggatg aggcactggt gccgattta   3720 cggacattcg tacagtccaa gaaaaatatc cttgtggatt atggactccg acgaatcaca  3780
ttcttgattg cccaagagaa agaatttccc aagttttca cattcagagc aagagatgag  3840
tttgcagaag atcgcattta ccgtcacttg gaacctgccc tggccttcca gctggaactc  3900
aaccggatgc gtaacttcga tctgaccgcc gtgccctgtg ccaaccacaa gatgcacctt  3960
tacctgggtg ctgccaaggt gaaggaaggt gtggaagtga cggaccatag gttcttcatc  4020
cgcgccatca tcaggcactc tgacctgatc acaaaggaag cctccttcga atacctgcag  4080
aacgagggtg agcggctact cctggaggcc atggacgagc tggaggtggc gttcaataac  4140
accagcgtgc gcaccgactg caaccacatc ttcctcaact tcgtgccac tgtcatcatg    4200 gaccccttca agatcgagga gtccgtgcgc tacatggtta tgcgctacgg cagccggctg  4260
tggaaactcc gtgtgctaca ggctgaggtc aagatcaaca tccgcagac caccaccggc  4320 agtgccgttc ccatccgcct gttcatcacc aatgagtcgg gctactacct ggacatcagc  4380
ctctacaaag aagtgactga ctccagatct ggaaatatca tgtttcactc cttcggcaac  4440
aagcaagggc cccagcacgg gatgctgatc aatactccct acgtcaccaa ggatctgctc  4500
caggccaagc gattccaggc ccagaccctg ggaaccacct acatctatga cttcccggaa  4560
atgttcaggc aggctctctt taaactgtgg ggctccccag acaagtatcc caaagacatc  4620
```

```
ctgacataca ctgaattagt gttggactct cagggccagc tgtgtggagat gaaccgactt      4680 cctggtggaa atgaggtggg catggtggcc ttcaaaatga ggtttaagac ccaggagtac      4740
ccggaaggac gggatgtgat cgtcatcggc aatgacatca cctttcgcat tggatccttt      4800
ggccctggag aggaccttct gtacctgcgg gcatccgaga tggcccgggc agagggcatt      4860
cccaaaattt acgtggcagc caacagtggc gcccgtattg gcatggcaga ggagatcaaa      4920
cacatgttcc acgtggcttg ggtggaccca gaagaccccc acaaaggatt taaatacctg      4980
tacctgactc cccaagacta caccagaatc agctccctga actccgtcca ctgtaaacac      5040
atcgaggaag gaggagagtc cagatacatg atcacggata tcatcgggaa ggatgatggc      5100
ttgggcgtgg agaatctgag gggctcaggc atgattgctg gggagtcctc tctggcttac      5160
gaagagatcg tcaccattag cttggtgacc tgccgagcca ttgggattgg ggcctacttg      5220
gtgaggctgg gccagcgagt gatccaggtg gagaattccc acatcatcct cacaggagca      5280
agtgctctca acaaggtcct gggaagagag gtctacacat ccaacaacca gctgggtggc      5340
gttcagatca tgcattacaa tggtgtctcc cacatcaccg tgccagatga ctttgagggg      5400 gttttatacca tcctggagtg gctgtcctat atgccaaagg ataatcacag ccctgtccct      5460
atcatcacac ccactgaccc cattgacaga gaaattgaat tcctcccatc cagagctccc      5520
tacgaccccc ggtggatgct gcaggaagg cctcacccaa ctctgaaggg aacgtggcag      5580
agcggattct ttgaccacgg cagtttcaag gaaatcatgg caccctgggc gcagaccgtg      5640
gtgacaggac gagcaaggct tgggggggatt cccgtgggag tgattgctgt ggagacacgg      5700
actgtggagg tggcagtccc tgcagaccct gccaacctgg attctgaggc caagataatt      5760
cagcaggcag acaggtgtg gttcccagac tcagcctaca aaccgccca ggccatcaag      5820 gacttcaacc gggagaagtt gccctgatg atctttgcca actggagggg gttctccggt      5880
ggcatgaaag acatgtatga ccaggtgctg aagtttggag cctacatcgt ggacggcctt      5940
agacaataca aacagcccat cctgatctat atcccgccct atgcggagct ccggggaggc      6000
tcctgggtgg tcatagatgc caccatcaac ccgctgtgca tagaaatgta tgcagacaaa      6060
gagagcaggg gtggtgttct ggaaccagag gggacagtgg agattaagtt ccgaaagaaa      6120
gatctgataa agtccatgag aaggatcgat ccagcttaca agaagctcat ggaacagcta      6180 gggaacctg atctctccga caaggaccga aggacctggg agggccggct aaaggctcgc      6240
gaggacctgc tgctcccat ctaccaccag gtggcggtgc agttcgccga cttccatgac      6300
acacccggcc ggatgctgga aagggcgtc atatctgaca tcctggagtg gaagaccgca      6360
cgcaccttcc tgtattggcg tctgcgccgc ctcctcctgg aggaccaggt caagcaggag      6420
atcctgcagg ccagcgggga gctgagtcac gtgcatatcc agtccatgct gcgtcgctgg      6480
ttcgtggaga cggaggggc tgtcaaggcc tacttgtggg acaacaacca ggtggtcgtg      6540
cagtggctga acagcactg gcaggcaggg gatggcccgc gctccaccat ccgtgagaac      6600
atcacgtacc tgaagcacga ctctgtcctc aagaccatcc gaggcctggt tgaagaaaac      6660
cccgaggtgg ccgtggactg tgtgatatac ctgagccagc acatcagccc agctgagcgg      6720
gcgcaggtcg ttcacctgct gtctaccatg acagcccgg cctccacc                    6768
```

<210> SEQ ID NO 4
<211> LENGTH: 2256
<212> TYPE: PRT
<213> ORGANISM: Homo sapiens

<400> SEQUENCE: 4

```
Met Ser Pro Ala Lys Cys Lys Ile Cys Phe Pro Asp Arg Glu Val Lys
  1               5                  10                  15

Pro Ser Met Ser Gly Leu His Leu Val Lys Arg Gly Arg Glu His Lys
             20                  25                  30

Lys Leu Asp Leu His Arg Asp Phe Thr Val Ala Ser Pro Ala Glu Phe
             35                  40                  45

Val Thr Arg Phe Gly Gly Asp Arg Val Ile Glu Lys Val Leu Ile Ala
     50                  55                  60

Asn Asn Gly Ile Ala Ala Val Lys Cys Met Arg Ser Ile Arg Arg Trp
 65                  70                  75                  80

Ala Tyr Glu Met Phe Arg Asn Glu Arg Ala Ile Arg Phe Val Val Met
                 85                  90                  95

Val Thr Pro Glu Asp Leu Lys Ala Asn Ala Glu Tyr Ile Lys Met Ala
            100                 105                 110

Asp His Tyr Val Pro Val Pro Gly Gly Pro Asn Asn Asn Asn Tyr Ala
            115                 120                 125

Asn Val Glu Leu Ile Val Asp Ile Ala Lys Arg Ile Pro Val Gln Ala
130                 135                 140

Val Trp Ala Gly Trp Gly His Ala Ser Glu Asn Pro Lys Leu Pro Glu
145                 150                 155                 160

Leu Leu Cys Lys Asn Gly Val Ala Phe Leu Gly Pro Pro Ser Glu Ala
                165                 170                 175

Met Trp Ala Leu Gly Asp Lys Ile Ala Ser Thr Val Val Ala Gln Thr
            180                 185                 190

Leu Gln Val Pro Thr Leu Pro Trp Ser Gly Ser Gly Leu Thr Val Glu
        195                 200                 205

Trp Thr Glu Asp Asp Leu Gln Gln Gly Lys Arg Ile Ser Val Pro Glu
        210                 215                 220

Asp Val Tyr Asp Lys Gly Cys Val Lys Asp Val Asp Glu Gly Leu Glu
225                 230                 235                 240

Ala Ala Glu Arg Ile Gly Phe Pro Leu Met Ile Lys Ala Ser Glu Gly
                245                 250                 255

Gly Gly Gly Lys Gly Ile Arg Lys Ala Glu Ser Ala Glu Asp Phe Pro
            260                 265                 270

Ile Leu Phe Arg Gln Val Gln Ser Glu Ile Pro Gly Ser Pro Ile Phe
        275                 280                 285

Leu Met Lys Leu Ala Gln His Ala Arg His Leu Glu Val Gln Ile Leu
        290                 295                 300

Ala Asp Gln Tyr Gly Asn Ala Val Ser Leu Phe Gly Arg Asp Cys Ser
305                 310                 315                 320

Ile Gln Arg Arg His Gln Lys Ile Val Glu Glu Ala Pro Ala Thr Ile
                325                 330                 335

Ala Pro Leu Ala Ile Phe Glu Phe Met Glu Gln Cys Ala Ile Arg Leu
            340                 345                 350

Ala Lys Thr Val Gly Tyr Val Ser Ala Gly Thr Val Glu Tyr Leu Tyr
        355                 360                 365

Ser Gln Asp Gly Ser Phe His Phe Leu Glu Leu Asn Pro Arg Leu Gln
        370                 375                 380

Val Glu His Pro Cys Thr Glu Met Ile Ala Asp Val Asn Leu Pro Ala
385                 390                 395                 400

Ala Gln Leu Gln Ile Ala Met Gly Val Pro Leu His Arg Leu Lys Asp
            405                 410                 415
```

-continued

```
Ile Arg Leu Leu Tyr Gly Glu Ser Pro Trp Gly Val Thr Pro Ile Ser
            420                 425                 430

Phe Glu Thr Pro Ser Asn Pro Pro Leu Ala Arg Gly His Val Ile Ala
            435                 440                 445

Ala Arg Ile Thr Ser Glu Asn Pro Asp Glu Gly Phe Lys Pro Ser Ser
            450                 455                 460

Gly Thr Val Gln Glu Leu Asn Phe Arg Ser Ser Lys Asn Val Trp Gly
465                 470                 475                 480

Tyr Phe Ser Val Ala Ala Thr Gly Gly Leu His Glu Phe Ala Asp Ser
                485                 490                 495

Gln Phe Gly His Cys Phe Ser Trp Gly Glu Asn Arg Glu Glu Ala Ile
                500                 505                 510

Ser Asn Met Val Val Ala Leu Lys Glu Leu Ser Ile Arg Gly Asp Phe
            515                 520                 525

Arg Thr Thr Val Glu Tyr Leu Ile Asn Leu Leu Glu Thr Glu Ser Phe
            530                 535                 540

Gln Asn Asn Asp Ile Asp Thr Gly Trp Leu Asp Tyr Leu Ile Ala Glu
545                 550                 555                 560

Lys Val Gln Ala Glu Lys Pro Asp Ile Met Leu Gly Val Val Cys Gly
                565                 570                 575

Ala Leu Asn Val Ala Asp Ala Met Phe Arg Thr Cys Met Thr Asp Phe
            580                 585                 590

Leu His Ser Leu Glu Arg Gly Gln Val Leu Pro Ala Asp Ser Leu Leu
            595                 600                 605

Asn Leu Val Asp Val Glu Leu Ile Tyr Gly Gly Val Lys Tyr Ile Leu
            610                 615                 620

Lys Val Ala Arg Gln Ser Leu Thr Met Phe Val Leu Ile Met Asn Gly
625                 630                 635                 640

Cys His Ile Glu Ile Asp Ala His Arg Leu Asn Asp Gly Gly Leu Leu
                645                 650                 655

Leu Ser Tyr Asn Gly Asn Ser Tyr Thr Thr Tyr Met Lys Glu Glu Val
            660                 665                 670

Asp Ser Tyr Arg Ile Thr Ile Gly Asn Lys Thr Cys Val Phe Glu Lys
            675                 680                 685

Glu Asn Asp Pro Thr Val Leu Arg Ser Pro Ser Ala Gly Lys Leu Thr
690                 695                 700

Gln Tyr Thr Val Glu Asp Gly Gly His Val Glu Ala Gly Ser Ser Tyr
705                 710                 715                 720

Ala Glu Met Glu Val Met Lys Met Ile Met Thr Leu Asn Val Gln Glu
                725                 730                 735

Arg Gly Arg Val Lys Tyr Ile Lys Arg Pro Gly Ala Val Leu Glu Ala
            740                 745                 750

Gly Cys Val Val Ala Arg Leu Glu Leu Asp Asp Pro Ser Lys Val His
            755                 760                 765

Pro Ala Glu Pro Phe Thr Gly Glu Leu Pro Ala Gln Gln Thr Leu Pro
770                 775                 780

Ile Leu Gly Glu Lys Leu His Gln Val Phe His Ser Val Leu Glu Asn
785                 790                 795                 800

Leu Thr Asn Val Met Ser Gly Phe Cys Leu Pro Glu Pro Val Phe Ser
                805                 810                 815

Ile Lys Leu Lys Glu Trp Val Gln Lys Leu Met Met Thr Leu Arg His
            820                 825                 830

Pro Ser Leu Pro Leu Leu Glu Leu Gln Glu Ile Met Thr Ser Val Ala
```

-continued

```
                835                 840                 845
Gly Arg Ile Pro Ala Pro Val Glu Lys Ser Val Arg Arg Val Met Ala
            850                 855                 860
Gln Tyr Ala Ser Asn Ile Thr Ser Val Leu Cys Gln Phe Pro Ser Gln
865                 870                 875                 880
Gln Ile Ala Thr Ile Leu Asp Cys His Ala Ala Thr Leu Gln Arg Lys
                885                 890                 895
Ala Asp Arg Glu Val Phe Phe Ile Asn Thr Gln Ser Ile Val Gln Leu
            900                 905                 910
Val Gln Arg Tyr Arg Ser Gly Ile Arg Gly Tyr Met Lys Thr Val Val
            915                 920                 925
Leu Asp Leu Leu Arg Arg Tyr Leu Arg Val Glu His His Phe Gln Gln
            930                 935                 940
Ala His Tyr Asp Lys Cys Val Ile Asn Leu Arg Glu Gln Phe Lys Pro
945                 950                 955                 960
Asp Met Ser Gln Val Leu Asp Cys Ile Phe Ser His Ala Gln Val Ala
                965                 970                 975
Lys Lys Asn Gln Leu Val Ile Met Leu Ile Asp Glu Leu Cys Gly Pro
            980                 985                 990
Asp Pro Ser Leu Ser Asp Glu Leu Ile Ser Ile Leu Asn Glu Leu Thr
            995                 1000                1005
Gln Leu Ser Lys Ser Glu His Cys Lys Val Ala Leu Arg Ala Arg Gln
    1010                1015                1020
Ile Leu Ile Ala Ser His Leu Pro Ser Tyr Glu Leu Arg His Asn Gln
1025                1030                1035                1040
Val Glu Ser Ile Phe Leu Ser Ala Ile Asp Met Tyr Gly His Gln Phe
                1045                1050                1055
Cys Pro Glu Asn Leu Lys Lys Leu Ile Leu Ser Glu Thr Thr Ile Phe
            1060                1065                1070
Asp Val Leu Pro Thr Phe Phe Tyr His Ala Asn Lys Val Val Cys Met
            1075                1080                1085
Ala Ser Leu Glu Val Tyr Val Arg Arg Gly Tyr Ile Ala Tyr Glu Leu
            1090                1095                1100
Asn Ser Leu Gln His Arg Gln Leu Pro Asp Gly Thr Cys Val Val Glu
1105                1110                1115                1120
Phe Gln Phe Met Leu Pro Ser Ser His Pro Asn Arg Met Thr Val Pro
            1125                1130                1135
Ile Ser Ile Thr Asn Pro Asp Leu Leu Arg His Ser Thr Glu Leu Phe
            1140                1145                1150
Met Asp Ser Gly Phe Ser Pro Leu Cys Gln Arg Met Gly Ala Met Val
            1155                1160                1165
Ala Phe Arg Arg Phe Glu Asp Phe Thr Arg Asn Phe Asp Glu Val Ile
            1170                1175                1180
Ser Cys Phe Ala Asn Val Pro Lys Asp Thr Pro Leu Phe Ser Glu Ala
1185                1190                1195                1200
Arg Thr Ser Leu Tyr Ser Glu Asp Asp Cys Lys Ser Leu Arg Glu Glu
                1205                1210                1215
Pro Ile His Ile Leu Asn Val Ser Ile Gln Cys Ala Asp His Leu Glu
                1220                1225                1230
Asp Glu Ala Leu Val Pro Ile Leu Arg Thr Phe Val Gln Ser Lys Lys
            1235                1240                1245
Asn Ile Leu Val Asp Tyr Gly Leu Arg Arg Ile Thr Phe Leu Ile Ala
            1250                1255                1260
```

-continued

```
Gln Glu Lys Glu Phe Pro Lys Phe Phe Thr Phe Arg Ala Arg Asp Glu
1265                1270                1275                1280

Phe Ala Glu Asp Arg Ile Tyr Arg His Leu Glu Pro Ala Leu Ala Phe
            1285                1290                1295

Gln Leu Glu Leu Asn Arg Met Arg Asn Phe Asp Leu Thr Ala Val Pro
                1300                1305                1310

Cys Ala Asn His Lys Met His Leu Tyr Leu Gly Ala Ala Lys Val Lys
            1315                1320                1325

Glu Gly Val Glu Val Thr Asp His Arg Phe Phe Ile Arg Ala Ile Ile
        1330                1335                1340

Arg His Ser Asp Leu Ile Thr Lys Glu Ala Ser Phe Glu Tyr Leu Gln
1345                1350                1355                1360

Asn Glu Gly Glu Arg Leu Leu Leu Glu Ala Met Asp Glu Leu Glu Val
                1365                1370                1375

Ala Phe Asn Asn Thr Ser Val Arg Thr Asp Cys Asn His Ile Phe Leu
            1380                1385                1390

Asn Phe Val Pro Thr Val Ile Met Asp Pro Phe Lys Ile Glu Glu Ser
        1395                1400                1405

Val Arg Tyr Met Val Met Arg Tyr Gly Ser Arg Leu Trp Lys Leu Arg
    1410                1415                1420

Val Leu Gln Ala Glu Val Lys Ile Asn Ile Arg Gln Thr Thr Thr Gly
1425                1430                1435                1440

Ser Ala Val Pro Ile Arg Leu Phe Ile Thr Asn Glu Ser Gly Tyr Tyr
            1445                1450                1455

Leu Asp Ile Ser Leu Tyr Lys Glu Val Thr Asp Ser Arg Ser Gly Asn
        1460                1465                1470

Ile Met Phe His Ser Phe Gly Asn Lys Gln Gly Pro Gln His Gly Met
    1475                1480                1485

Leu Ile Asn Thr Pro Tyr Val Thr Lys Asp Leu Leu Gln Ala Lys Arg
    1490                1495                1500

Phe Gln Ala Gln Thr Leu Gly Thr Thr Tyr Ile Tyr Asp Phe Pro Glu
1505                1510                1515                1520

Met Phe Arg Gln Ala Leu Phe Lys Leu Trp Gly Ser Pro Asp Lys Tyr
            1525                1530                1535

Pro Lys Asp Ile Leu Thr Tyr Thr Glu Leu Val Leu Asp Ser Gln Gly
        1540                1545                1550

Gln Leu Val Glu Met Asn Arg Leu Pro Gly Gly Asn Glu Val Gly Met
        1555                1560                1565

Val Ala Phe Lys Met Arg Phe Lys Thr Gln Glu Tyr Pro Glu Gly Arg
    1570                1575                1580

Asp Val Ile Val Ile Gly Asn Asp Ile Thr Phe Arg Ile Gly Ser Phe
1585                1590                1595                1600

Gly Pro Gly Glu Asp Leu Leu Tyr Leu Arg Ala Ser Glu Met Ala Arg
            1605                1610                1615

Ala Glu Gly Ile Pro Lys Ile Tyr Val Ala Ala Asn Ser Gly Ala Arg
            1620                1625                1630

Ile Gly Met Ala Glu Glu Ile Lys His Met Phe His Val Ala Trp Val
        1635                1640                1645

Asp Pro Glu Asp Pro His Lys Gly Phe Lys Tyr Leu Tyr Leu Thr Pro
1650                1655                1660

Gln Asp Tyr Thr Arg Ile Ser Ser Leu Asn Ser Val His Cys Lys His
1665                1670                1675                1680
```

-continued

Ile Glu Glu Gly Gly Glu Ser Arg Tyr Met Ile Thr Asp Ile Ile Gly
            1685                1690                1695

Lys Asp Asp Gly Leu Gly Val Glu Asn Leu Arg Gly Ser Gly Met Ile
        1700                1705                1710

Ala Gly Glu Ser Ser Leu Ala Tyr Glu Ile Val Thr Ile Ser Leu
        1715                1720                1725

Val Thr Cys Arg Ala Ile Gly Ile Gly Ala Tyr Leu Val Arg Leu Gly
        1730                1735                1740

Gln Arg Val Ile Gln Val Glu Asn Ser His Ile Ile Leu Thr Gly Ala
1745                1750                1755                1760

Ser Ala Leu Asn Lys Val Leu Gly Arg Glu Val Tyr Thr Ser Asn Asn
                1765                1770                1775

Gln Leu Gly Gly Val Gln Ile Met His Tyr Asn Gly Val Ser His Ile
            1780                1785                1790

Thr Val Pro Asp Asp Phe Glu Gly Val Tyr Thr Ile Leu Glu Trp Leu
        1795                1800                1805

Ser Tyr Met Pro Lys Asp Asn His Ser Pro Val Pro Ile Ile Thr Pro
        1810                1815                1820

Thr Asp Pro Ile Asp Arg Glu Ile Glu Phe Leu Pro Ser Arg Ala Pro
1825                1830                1835                1840

Tyr Asp Pro Arg Trp Met Leu Ala Gly Arg Pro His Pro Thr Leu Lys
                1845                1850                1855

Gly Thr Trp Gln Ser Gly Phe Phe Asp His Gly Ser Phe Lys Glu Ile
            1860                1865                1870

Met Ala Pro Trp Ala Gln Thr Val Val Thr Gly Arg Ala Arg Leu Gly
        1875                1880                1885

Gly Ile Pro Val Gly Val Ile Ala Val Glu Thr Arg Thr Val Glu Val
        1890                1895                1900

Ala Val Pro Ala Asp Pro Ala Asn Leu Asp Ser Glu Ala Lys Ile Ile
1905                1910                1915                1920

Gln Gln Ala Gly Gln Val Trp Phe Pro Asp Ser Ala Tyr Lys Thr Ala
                1925                1930                1935

Gln Ala Ile Lys Asp Phe Asn Arg Glu Lys Leu Pro Leu Met Ile Phe
            1940                1945                1950

Ala Asn Trp Arg Gly Phe Ser Gly Gly Met Lys Asp Met Tyr Asp Gln
            1955                1960                1965

Val Leu Lys Phe Gly Ala Tyr Ile Val Asp Gly Leu Arg Gln Tyr Lys
        1970                1975                1980

Gln Pro Ile Leu Ile Tyr Ile Pro Pro Tyr Ala Glu Leu Arg Gly Gly
1985                1990                1995                2000

Ser Trp Val Val Ile Asp Ala Thr Ile Asn Pro Leu Cys Ile Glu Met
                2005                2010                2015

Tyr Ala Asp Lys Glu Ser Arg Gly Gly Val Leu Glu Pro Glu Gly Thr
            2020                2025                2030

Val Glu Ile Lys Phe Arg Lys Lys Asp Leu Ile Lys Ser Met Arg Arg
        2035                2040                2045

Ile Asp Pro Ala Tyr Lys Lys Leu Met Glu Gln Leu Gly Glu Pro Asp
        2050                2055                2060

Leu Ser Asp Lys Asp Arg Lys Asp Leu Glu Gly Arg Leu Lys Ala Arg
2065                2070                2075                2080

Glu Asp Leu Leu Leu Pro Ile Tyr His Gln Val Ala Val Gln Phe Ala
                2085                2090                2095

Asp Phe His Asp Thr Pro Gly Arg Met Leu Glu Lys Gly Val Ile Ser

-continued

```
                 2100            2105            2110
Asp Ile Leu Glu Trp Lys Thr Ala Arg Thr Phe Leu Tyr Trp Arg Leu
            2115            2120            2125
Arg Arg Leu Leu Leu Glu Asp Gln Val Lys Gln Glu Ile Leu Gln Ala
        2130            2135            2140
Ser Gly Glu Leu Ser His Val His Ile Gln Ser Met Leu Arg Arg Trp
2145            2150            2155            2160
Phe Val Glu Thr Glu Gly Ala Val Lys Ala Tyr Leu Trp Asp Asn Asn
            2165            2170            2175
Gln Val Val Gln Trp Leu Gly Gln His Trp Gln Ala Gly Asp Gly
        2180            2185            2190
Pro Arg Ser Thr Ile Arg Glu Asn Ile Thr Tyr Leu Lys His Asp Ser
            2195            2200            2205
Val Leu Lys Thr Ile Arg Gly Leu Val Glu Glu Asn Pro Glu Val Ala
        2210            2215            2220
Val Asp Cys Val Ile Tyr Leu Ser Gln His Ile Ser Pro Ala Glu Arg
2225            2230            2235            2240
Ala Gln Val Val His Leu Leu Ser Thr Met Asp Ser Pro Ala Ser Thr
            2245            2250            2255

<210> SEQ ID NO 5
<211> LENGTH: 20
<212> TYPE: DNA
<213> ORGANISM: Artificial Sequence
<220> FEATURE:
<223> OTHER INFORMATION: oligonucleotide

<400> SEQUENCE: 5
gcgaagtaaa gccgagcatg                                                 20

<210> SEQ ID NO 6
<211> LENGTH: 10
<212> TYPE: PRT
<213> ORGANISM: Artificial Sequence
<220> FEATURE:
<223> OTHER INFORMATION: peptide

<400> SEQUENCE: 6

Asp Arg Glu Val Lys Pro Ser Met Ser Gly
 1               5                  10

<210> SEQ ID NO 7
<211> LENGTH: 27
<212> TYPE: DNA
<213> ORGANISM: Artificial Sequence
<220> FEATURE:
<223> OTHER INFORMATION: oligonucleotide

<400> SEQUENCE: 7
caagtgcaag atctgtttcc ctgatcg                                         27

<210> SEQ ID NO 8
<211> LENGTH: 27
<212> TYPE: DNA
<213> ORGANISM: Artificial Sequence
<220> FEATURE:
<223> OTHER INFORMATION: oligonucleotide

<400> SEQUENCE: 8
ccggaagttt agggttttct gaagcat                                         27
```

```
<210> SEQ ID NO 9
<211> LENGTH: 40
<212> TYPE: DNA
<213> ORGANISM: Artificial Sequence
<220> FEATURE:
<223> OTHER INFORMATION: oligonucleotide

<400> SEQUENCE: 9
gagcccggtg ggattggcct gcggggtggt caacatgagt                          40

<210> SEQ ID NO 10
<211> LENGTH: 33
<212> TYPE: DNA
<213> ORGANISM: Artificial Sequence
<220> FEATURE:
<223> OTHER INFORMATION: oligonucleotide

<400> SEQUENCE: 10
tcaggtggag gccgggctgt ccatggtaga cag                                 33

<210> SEQ ID NO 11
<211> LENGTH: 77
<212> TYPE: DNA
<213> ORGANISM: Artificial Sequence
<220> FEATURE:
<223> OTHER INFORMATION: oligonucleotide

<400> SEQUENCE: 11
gcctaggtaa tgagtcctgc caagtgcaag atctgtttcc ctgatcgcga agtaaagccg    60
agcatgtcgg gactcca                                                  77

<210> SEQ ID NO 12
<211> LENGTH: 18
<212> TYPE: DNA
<213> ORGANISM: Artificial Sequence
<220> FEATURE:
<223> OTHER INFORMATION: oligonucleotide

<400> SEQUENCE: 12
ggccggtgct tcctcaac                                                 18

<210> SEQ ID NO 13
<211> LENGTH: 39
<212> TYPE: DNA
<213> ORGANISM: Artificial Sequence
<220> FEATURE:
<223> OTHER INFORMATION: oligonucleotide

<400> SEQUENCE: 13
gcctaggtaa tggtcttgct tctttgtcta tcttgtctg                          39

<210> SEQ ID NO 14
<211> LENGTH: 28
<212> TYPE: DNA
<213> ORGANISM: Artificial Sequence
<220> FEATURE:
<223> OTHER INFORMATION: oligonucleotide

<400> SEQUENCE: 14
accggtggtg gaggccgggc tgtccatg                                      28

<210> SEQ ID NO 15
<211> LENGTH: 41
<212> TYPE: DNA
<213> ORGANISM: Artificial Sequence
<220> FEATURE:
```

```
<223> OTHER INFORMATION: oligonucleotide

<400> SEQUENCE: 15
gcctaggata atggatgaac catctccctt ggcccaacct c                    41

<210> SEQ ID NO 16
<211> LENGTH: 34
<212> TYPE: DNA
<213> ORGANISM: Artificial Sequence
<220> FEATURE:
<223> OTHER INFORMATION: oligonucleotide

<400> SEQUENCE: 16
aggacgcgca atttccacag gcgacttcca tacc                            34

<210> SEQ ID NO 17
<211> LENGTH: 31
<212> TYPE: DNA
<213> ORGANISM: Artificial Sequence
<220> FEATURE:
<223> OTHER INFORMATION: oligonucleotide

<400> SEQUENCE: 17
gagtcccaca ttccctgagg caggtcacac g                               31

<210> SEQ ID NO 18
<211> LENGTH: 30
<212> TYPE: DNA
<213> ORGANISM: Artificial Sequence
<220> FEATURE:
<223> OTHER INFORMATION: oligonucleotide

<400> SEQUENCE: 18
accggtcgtg aagggggaat ccattgtgga                                 30

<210> SEQ ID NO 19
<211> LENGTH: 26
<212> TYPE: DNA
<213> ORGANISM: Artificial Sequence
<220> FEATURE:
<223> OTHER INFORMATION: oligonucleotide

<400> SEQUENCE: 19
ttatctgacc acaggtgaag ctgaga                                     26

<210> SEQ ID NO 20
<211> LENGTH: 27
<212> TYPE: DNA
<213> ORGANISM: Artificial Sequence
<220> FEATURE:
<223> OTHER INFORMATION: oligonucleotide

<400> SEQUENCE: 20
gctccggaag tttagggttt tctaaag                                    27

<210> SEQ ID NO 21
<211> LENGTH: 20
<212> TYPE: DNA
<213> ORGANISM: Artificial Sequence
<220> FEATURE:
<223> OTHER INFORMATION: oligonucleotide

<400> SEQUENCE: 21
gaccacaggt gaagctgaga                                            20
```

```
<210> SEQ ID NO 22
<211> LENGTH: 19
<212> TYPE: DNA
<213> ORGANISM: Artificial Sequence
<220> FEATURE:
<223> OTHER INFORMATION: oligonucleotide

<400> SEQUENCE: 22
gtgttcccgt cccctcttc                                              19

<210> SEQ ID NO 23
<211> LENGTH: 18
<212> TYPE: DNA
<213> ORGANISM: Artificial Sequence
<220> FEATURE:
<223> OTHER INFORMATION: oligonucleotide

<400> SEQUENCE: 23
acatgctcgg cctcatag                                               18

<210> SEQ ID NO 24
<211> LENGTH: 24
<212> TYPE: DNA
<213> ORGANISM: Artificial Sequence
<220> FEATURE:
<223> OTHER INFORMATION: oligonucleotide

<400> SEQUENCE: 24
aagtgcaaga tctgtttccc tgat                                        24

<210> SEQ ID NO 25
<211> LENGTH: 19
<212> TYPE: DNA
<213> ORGANISM: Artificial Sequence
<220> FEATURE:
<223> OTHER INFORMATION: oligonucleotide

<400> SEQUENCE: 25
caggtggagt cccgacatg                                              19

<210> SEQ ID NO 26
<211> LENGTH: 17
<212> TYPE: DNA
<213> ORGANISM: Artificial Sequence
<220> FEATURE:
<223> OTHER INFORMATION: oligonucleotide

<400> SEQUENCE: 26
ctcggcttta cttcgcg                                                17
```

ALTERNATIVELY SPLICED ISOFORM OF ACETYL-COA CARBOXYLASE 2 (ACC2)

This application claims priority to U.S. Provisional Patent Application Ser. No. 60/577,234 filed on Jun. 4, 2004, which is incorporated by reference herein in its entirety.

BACKGROUND OF THE INVENTION

The references cited herein are not admitted to be prior art to the claimed invention.

Fat is a major energy reserve and energy source in humans. Fatty acid metabolism is highly regulated so that synthesis and oxidation is related to physiological demands. Acetyl coenzyme A carboxylase (ACC) is utilized by cells to control fatty acid levels. ACC systems are responsive to various internal and external signals, such as diet, development, hormones, and genetics. Though the two isozymes of ACC both catalyze the same reaction, ACC1 and ACC2 appear to have distinct functions. ACC1 catalyzes the rate limiting step in fatty acid synthesis while ACC2 controls fatty acid oxidation. Abnormal fatty acid metabolism not only affects energy production, but also development of diseases such as cardiovascular disease, diabetes, and obesity (reviewed in Kim, 1997, Annu. Rev. Nutr. 17:77–99; Rasmussen and Wolfe, 1999, Annu. Rev. Nutr. 19:463–484).

ACC, a biotin-containing enzyme, catalyzes the carboxylation of acetyl-CoA to malonyl-CoA in a two-step reaction. Malonyl-CoA is the substrate for long-chain fatty acid synthesis along with acetyl CoA and NADPH, which is catalyzed by fatty acid synthase in a series of enzyme reactions, resulting in palmitic acid. Malonyl CoA also regulates fatty acid B-oxidation in the mitochondria through its inhibition of carnitine palmitoyl transferase 1 (CPT1). CPT1, embedded in the mitochondrial outer membrane, is the rate-limiting enzyme in mitochondrial uptake of fatty acids. Fatty acyl CoA, converted from fatty acids by fatty acyl CoA synthetase, is taken up by CPT1, the first step in the carnitine shuttle into the mitochondria. Once inside the mitochondria, fatty acyl CoA undergoes β-oxidation to produce acetyl-CoA. Acetyl-CoA may then enter the Kreb's cycle and contribute to ATP production via the electron transport chain (reviewed in Kim, 1997, Annu. Rev. Nutri. 17:77–99; Munday and Hemingway, 1999, Adv. Enzyme Regul. 39:205–234; Dyck and Lopaschuk, 2002, J. Mol. Cell. Cardiol. 34:1099–1109).

Human ACC1 is a 265 kDa protein with 2,346 amino acids, encoded by a gene on chromosome 17 (Abu-Elheiga et al., 1995, Proc. Natl. Acad. Sci. USA, 92:4011–4015). Human ACC2 gene is localized on chromosome 12 (Ullrich et al., 1997, Cytogenet. Cell Genet. 77:176–177). The ACC2 mRNA transcript (AJ575592) consists of 51 coding exons which encode a 2,458 amino acid protein. The domain structure of the catalytic regions of both ACC1 and ACC2 are nearly identical, with 85% homology. The functional sites consist of ATP, biotin (carboxylation), and acyl-CoA binding sites, and key phosphorylation sites. The major difference between the two isoforms lies in a unique N-terminal sequence of about 150 amino acids in ACC2, which may be related to its function in the mitochondria (reviewed in Kim, 1997, Annu. Rev. Nutr. 17:77–99; Munday and Hemingway, 1999, Adv. Enzyme Regul. 39:205–234). ACC2 homologs have been identified in other species. For example, the human ACC2 protein has 80% identity to the rat ACC2 (Abe et al., 1998, Biochim. Biophys. Acta. 1398: 347–352). ACC1 is the predominant isoform in lipogenic tissue, such as white adipose tissue. However, in oxidative tissues such as the heart and skeletal muscle, ACC2 is the major form expressed. Both ACC1 and ACC2 are expressed in the liver, where both fatty acid synthesis and oxidation take place (Trumble et al., 1995, Eur. J. Biochem. 231: 192–198; Bianchi et al., 1990, J. Biol. Chem. 265:1502–1509; Abu-Elheiga et al, 1997, J. Biol. Chem. 272:10669–10677; Ha et al., 1996, Proc. Natl. Acad. Sci. USA 93:11466–11470).

The unique N-terminal sequence of ACC2 appears rich in hydroxy and basic amino acids, which is typical for transit peptides that are targeted to the mitochondria. However, the ACC2 N-terminal sequence is interrupted by proline residues (17 proline residues between positions 31 and 147). Furthermore, the basic amino acids are counterbalanced by a comparable number of acidic aminoacids. These aforementioned features, along with the length of the N-terminal region, do not support the amphiphilic secondary structure of a mitochondrial import protein. On the whole, the N-terminal sequence of ACC2 has hydrophilic features, except for the first 25 amino acids which are hydrophobic. Instead, it has been suggested that the hydrophobic region (first 25 amino acids) anchors ACC2 to the mitochondrial outer membrane, near the malonyl CoA binding site of CPT1 (Ha et al., Proc. Natl. Acad. Sci. USA 93:11466–11470). Phosphorylation of the hydroxy amino acids in the N-terminus may also influence anchoring of ACC2 to the mitochondrial outer membrane (Ha et al., 1996, Proc. Natl. Acad. Sci. USA 93:11466–11470; reviewed in Kim, 1997, Annu. Rev. Nutr. 17:77–99; Munday and Hemingway, 1999, Adv. Enzyme Regul. 39:205–234). Abu-Elheiga et al. (2000, Proc. Natl. Acad. Sci. USA 97:1444–1449) using chimeric reporter proteins, demonstrated that ACC2 associated with the mitochondria, the ACC2 N-terminal sequence directed green fluorescent protein (GFP) to the mitochondria, and an ACC2 N-terminus-GFP fusion protein frequently co-localized on the mitochondria with CPT1. ACC1, which lacks the hydrophobic N-terminal sequence, has been shown to localize in the cytosol (Abu-Elheiga, 2000, Proc. Natl. Acad. Sci. USA 97:1444–1449).

ACC2 activity is regulated by a variety of mechanisms. Phosphorylation of key serine residues by 5'-AMP-activated kinase (AMPK) results in inactivation of both ACC1 and ACC2, which decreases malonyl-CoA levels and results in inhibition of fatty acid synthesis and activation of fatty acid oxidation, respectively (Davies et al., 1990, Eur. J. Biochem. 187:183–190; Winder et al., 1997, J. Appl. Physiol. 82:219–225). AMPK is activated by cellular stress that depletes ATP stores (reviewed in Hardie and Hawley, 2001, Bioessays 23:1112–1119). ACC2 may also be allosterically activated by citrate (Saha et al., 1999, Am. J. Physiol. 276:E1030–E1037; reviewed in Ruderman et al., 1999, Am. J. Physiol. 276: E1–E18). However, ACC2 activation by citrate is inhibited by AMPK phosphorylation of ACC2 (Vawas et al., 1997, J. Biol. Chem. 272:13255–13261). Recently, Minokoshi et al. (2002, Nature 415:339–343) demonstrated that the hormone leptin could suppress ACC2 activity through its activation of AMPK in skeletal muscle.

Inhibitors of ACC isozymes have also been identified. CP-610431 and its more stable analog, CP-640186, have been shown to inhibit both ACC1 and ACC2. These compounds reduced malonyl-CoA levels in liver, heart, and skeletal muscle; reduced fatty acid synthesis in cultured liver cells and in the liver and adipose tissue of experimental animals; and increased fatty acid oxidation in cultured skeletal muscle cells and tissue slices (Harwood et al., 2003, J. Biol. Chem. 278:37099–37111). ESP 55016 has been shown to favorably alter serum lipid levels in the rat model of diabetic dyslipidemia. ESP 55016 inhibited fatty acid synthesis and enhanced fatty acid oxidation, and a naturally occurring CoA derivative of ESP 55016 inhibited ACC in a concentration dependent manner (Cramer et al., Apr. 21, 2004 J. Lipid Res. Epub ahead of print). Commercial herbicides, such as haloxyfop, diclofop, and sethoxydim are potent inhibitors of ACCs from plants. Zhang et al. (2004, Proc. Natl. Acad. Sci. USA 101:5910–5915) revealed the molecular mechanism for the inhibition of the carboxyltransferase domain of ACC by haloxyfop and diclofop, which may facilitate drug development for human ACCs.

Studies of ACC2 knockout mice have indicated that ACC2-deficient mice have a higher fatty acid oxidation rate and 50% less fat in their adipose tissue. Fatty acid oxidation in these mutant mice was also non-responsive to insulin (Abu-Elheiga et al., 2001, Science 291:2613–2616). Further study of these knockout mice showed that ACC2-deficiency was protective against obesity and diabetes induced by high-fat/high-carbohydrate diets, suggesting that ACC2 may be an attractive drug target for obesity and related diseases (Abu-Elheiga et al., 2003, Proc. Natl. Acad. Sci. USA 100:10207–10212).

Defects in fatty acid metabolism have been associated with disease. Fatty acid oxidation disorders may have a wide variety of symptoms, such as cardiomyopathy, arrhythmias, myopathy, hypoketotic hypoglycaemia, liver disease, sudden infant death, and peripheral neuropathy (Den Boer et al., 2003, J. Pediatr. 142: 684–689; reviewed in Gregersen et al., 2004, Eur. J. Biochem. 271:470–482; Sim et al, 2002, Clin. Chim. Acta 323:37–58; Olpin, 2004, Prostaglandins Leukot. Essent. Fatty Acids 70:293–308; Guertl et al., 2000, Int. J. Exp. Pathol. 81:349–372). Features of metabolic syndrome include insulin resistance, obesity, hypertension, and dyslipidaemia. Metabolic syndrome also confers predisposition to type-2 diabetes and atherosclerosis. Dysregulation of fatty acid metabolism has been implicated in metabolic syndrome, and development of therapeutic approaches has targeted ACC (reviewed in Moller, 2001, Nature 414:821–827; Ruderman and Prentki, 2004, Nat. Rev. Drug Discov. 3:340–351). High rates of fatty acid oxidation due to a decrease in malonyl-CoA may also contribute to ischemic heart damage, and targeting enzymes involved in malonyl-CoA control may improve cardiac efficiency in ischemic hearts (Kudo et al., 1995, J. Biol. Chem. 270: 17513–17520; reviewed in Dyck and Lopaschuk, 2002, J. Mol. Cell. Cardiol. 34:1099–1109).

Abu-Elheiga et al. (1997, J. Biol. Chem. 272:10669–10677) identified an additional ACC2 isoform of 270 kDa in human liver. Sequencing of this isoform revealed that it is missing 101 amino acids in the region between $Arg^{1114}$ and $Asp^{1215}$. Experimental evidence also suggests that two ACC2 mRNA transcripts exist with different 5'-untranslated regions resulting from alternative usage of promoters I and II. Alternative usage of promoters I and II appears to result from alternative splicing using either exon 1A or exon 1B, respectively (Lee et al., 2001, J. Biol. Chem. 276:2576–2585; Oh et al., 2003, J. Biol. Chem. 278:28410–28417). Transcription using promoter II appears to be regulated by muscle regulatory factors in skeletal muscle and sterol regulatory element-binding protein-1 in the liver.

Because of the multiple therapeutic values of drugs targeting fatty acid metabolism enzymes, including ACC2, there is a need in the art for compounds that selectively bind to isoforms of ACC. The present invention is directed towards a novel ACC2 isoform (ACC2) and uses thereof.

BRIEF DESCRIPTION OF THE FIGURES

In FIG. 1B, in the case of the ACC2sv1 splice junction sequence (SEQ ID NO 1), the nucleotides shown in italics represent the 20 nucleotides at the 3' end of exon 1A and the nucleotides shown in underline represent the 20 nucleotides at the 5' end of exon 2.

SUMMARY OF THE INVENTION

Figure 1:
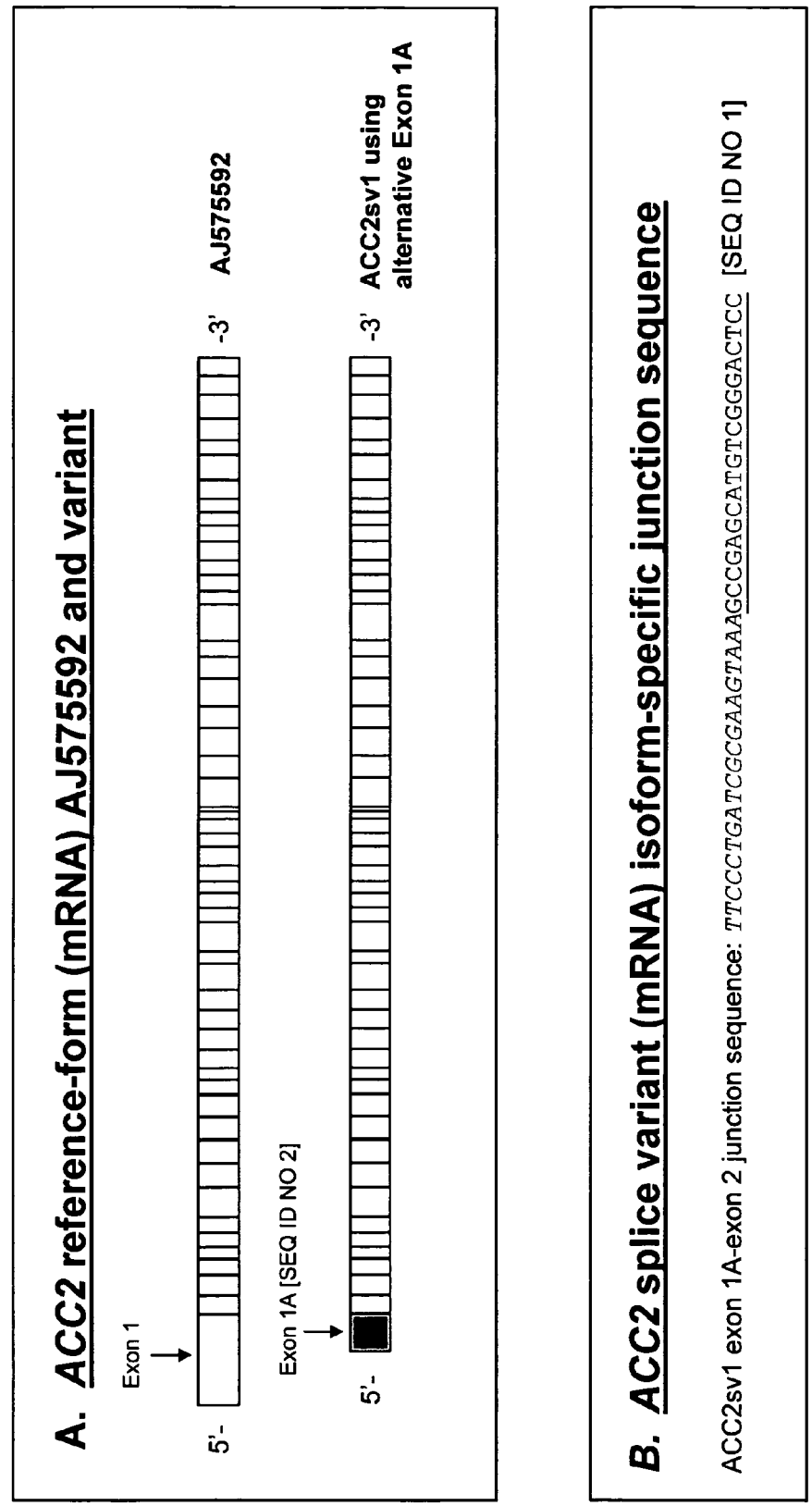
FIG. 1A illustrates the exon structure of human ACC2 mRNA corresponding to the known reference form of ACC2 mRNA (labeled AJ575592) and the exon structure corresponding to the inventive splice variant transcript (labeled ACC2sv1).
FIG. 1B depicts the nucleotide sequences of the exon junctions resulting from the splicing of exon 1A to exon 2 in the case of ACC2sv1 mRNA (SEQ ID NO 1), where the sequence of exon 1A is set forth in SEQ ID NO 2.

RT-PCR and DNA sequence analysis, and real-time quantitative PCR have been used to identify and confirm the presence of a novel splice variant of human ACC2 mRNA.

More specifically, the present invention features polynucleotides encoding a different protein isoform of ACC2. A polynucleotide sequence encoding ACC2sv1 is provided by SEQ ID NO 3. An amino acid sequence for ACC2sv1 is provided by SEQ ID NO 4.

Thus, a first aspect of the present invention describes a purified ACC2sv1 encoding nucleic acid. The ACC2sv1 encoding nucleic acid comprises SEQ ID NO 3 or the complement thereof. Reference to the presence of one region does not indicate that another region is not present. For example, in different embodiments the inventive nucleic acid can comprise, consist, or consist essentially of an encoding nucleic acid sequence of SEQ ID NO 3.

Another aspect of the present invention describes a purified ACC2sv1 polypeptide that can comprise, consist or consist essentially of the amino acid sequence of SEQ ID NO 4.

Another aspect of the present invention describes ACC2sv1 expression vectors. In one embodiment of the invention, the inventive ACC2sv1 expression vector comprises a nucleotide sequence encoding a polypeptide comprising, consisting, or consisting essentially of SEQ ID NO 4, wherein the nucleotide sequence is transcriptionally coupled to an exogenous promoter.

Alternatively, the nucleotide sequence comprises, consists, or consists essentially of SEQ ID NO 3, and is transcriptionally coupled to an exogenous promoter.

Another aspect of the present invention describes recombinant cells comprising expression vectors comprising, consisting, or consisting essentially of the above-described sequences and the promoter is recognized by an RNA polymerase present in the cell. Another aspect of the present invention describes a recombinant cell made by a process comprising the step of introducing into the cell an expression vector comprising a nucleotide sequence comprising, consisting, or consisting essentially of SEQ ID NO 3, or a nucleotide sequence encoding a polypeptide comprising, consisting, or consisting essentially of an amino acid sequence of SEQ ID NO 4, wherein the nucleotide sequence is transcriptionally coupled to an exogenous promoter. The expression vector can be used to insert recombinant nucleic acid into the host genome or can exist as an autonomous piece of nucleic acid.

Another aspect of the present invention describes a method of producing ACC2sv1 polypeptide comprising SEQ ID NO 4. The method involves the step of growing a recombinant cell containing an inventive expression vector under conditions wherein the polypeptide is expressed from the expression vector.

Another aspect of the present invention features a purified antibody preparation comprising an antibody that binds selectively to ACC2sv1 as compared to one or more ACC isoform polypeptides that are not ACC2sv1.

Another aspect of the present invention provides a method of screening for a compound that binds to ACC2sv1 or fragments thereof. In one embodiment, the method comprises the steps of: (a) expressing a polypeptide comprising the amino acid sequence of SEQ ID NO 4 or a fragment thereof from recombinant nucleic acid; (b) providing to said polypeptide a labeled ACC2 ligand that binds to said polypeptide and a test preparation comprising one or more test compounds; (c) and measuring the effect of said test preparation on binding of said test preparation to said polypeptide comprising SEQ ID NO 4.

In another embodiment of the method, a compound is identified that binds selectively to ACC2sv1 polypeptide as compared to one or more ACC isoform polypeptides that are not ACC2sv1. This method comprises the steps of: providing an ACC2sv1 polypeptide comprising SEQ ID NO 4; providing an ACC isoform polypeptide that is not ACC2sv1; contacting said ACC2sv1 polypeptide and said ACC isoform polypeptide that is not ACC2sv1 with a test preparation comprising one or more test compounds; and determining the binding of said test preparation to said ACC2sv1 polypeptide and to said ACC isoform polypeptide that is not ACC2sv1, wherein a test preparation that binds to said ACC2sv1 polypeptide but does not bind to said ACC isoform polypeptide that is not ACC2sv1 contains a compound that selectively binds said ACC2sv1 polypeptide.

In another embodiment of the invention, a method is provided for screening for a compound able to bind to or interact with a ACC2sv1 protein or a fragment thereof comprising the steps of: expressing an ACC2sv1 polypeptide comprising SEQ ID NO 4 or a fragment thereof from a recombinant nucleic acid; providing to said polypeptide a labeled ACC2 ligand that binds to said polypeptide and a test preparation comprising one or more compounds; and measuring the effect of said test preparation on binding of said labeled ACC2 ligand to said polypeptide, wherein a test preparation that alters the binding of said labeled ACC2 ligand to said polypeptide contains a compound that binds to or interacts with said polypeptide.

Another aspect of the present invention provides a method of screening for a compound that binds to one or more ACC isoform polypeptides that are not ACC2sv1. This method comprises the steps of: providing an ACC2sv1 polypeptide comprising SEQ ID NO 4; providing an ACC isoform polypeptide that is not ACC2sv1; contacting said ACC2sv1 polypeptide and ACC isoform polypeptide that is not ACC2sv1 with a test preparation comprising one or more test compounds; and determining the binding of said test preparation to said ACC2sv1 polypeptide and to said ACC isoform polypeptide that is not ACC2sv1, wherein a test preparation that binds to said ACC isoform polypeptide that is not ACC2sv1 but not to said ACC2sv1 polypeptide contains a compound that selectively binds said ACC2 isoform polypeptide.

Other features and advantages of the present invention are apparent from the additional descriptions provided herein, including the different examples. The provided examples illustrate different components and methodology useful in practicing the present invention. The examples do not limit the claimed invention. Based on the present disclosure the skilled artisan can identify and employ other components and methodology useful for practicing the present invention.

DEFINITIONS

Unless defined otherwise, all technical and scientific terms used herein have the meaning commonly understood by one of ordinary skill in the art to which this invention belongs.

As used herein, "ACC2" refers to acetyl Coenzyme A carboxylase 2 (AJ575592), also known as acetyl Coenzyme A carboxylase-beta (ACACB or ACCB). In contrast, reference to an ACC2 isoform includes AJ575592 and other polypeptide isoform variants of ACC2.

As used herein, "ACC2sv1" refers to a splice variant isoform of human ACC2 protein, wherein the splice variant has the amino acid sequence set forth in SEQ ID NO 4 (for ACC2sv1).

As used herein, "ACC2" refers to polynucleotides encoding ACC2.

As used herein, "ACC2sv1" refers to polynucleotides that are identical to ACC2 encoding polynucleotides, except that the sequences represented by exon 1 of the ACC2 messenger RNA are not present in ACC2sv1 and are replaced with an alternative exon 1A. "Exon 1A" refers to the polynucleotides encoding the portion of intron 1 retained in ACC2sv1. The polynucleotide sequence of exon 1A is set forth in SEQ ID NO 2.

As used herein, "ACC" is any isoform of any acetyl Coenzyme A carboxylase from any organism, including but not limited to human acetyl Coenzyme A carboxylase 1 (ACC1), also known as acetyl Coenzyme A carboxylase-alpha (ACACA or ACCA), and human ACC2.

As used herein, an "isolated nucleic acid" is a nucleic acid molecule that exists in a physical form that is nonidentical to any nucleic acid molecule of identical sequence as found in nature; "isolated" does not require, although it does not prohibit, that the nucleic acid so described has itself been physically removed from its native environment. For example, a nucleic acid can be said to be "isolated" when it includes nucleotides and/or internucleoside bonds not found in nature. When instead composed of natural nucleosides in phosphodiester linkage, a nucleic acid can be said to be "isolated" when it exists at a purity not found in nature, where purity can be adjudged with respect to the presence of nucleic acids of other sequence, with respect to the presence of proteins, with respect to the presence of lipids, or with respect to the presence of any other component of a biological cell, or when the nucleic acid lacks sequence that flanks an otherwise identical sequence in an organism's genome, or when the nucleic acid possesses sequence not identically present in nature. As so defined, "isolated nucleic acid" includes nucleic acids integrated into a host cell chromosome at a heterologous site, recombinant fusions of a native fragment to a heterologous sequence, recombinant vectors present as episomes or as integrated into a host cell chromosome.

A "purified nucleic acid" represents at least 10% of the total nucleic acid present in a sample or preparation. In preferred embodiments, the purified nucleic acid represents at least about 50%, at least about 75%, or at least about 95% of the total nucleic acid in a isolated nucleic acid sample or preparation. Reference to "purified nucleic acid" does not require that the nucleic acid has undergone any purification and may include, for example, chemically synthesized nucleic acid that has not been purified.

The phrases "isolated protein", "isolated polypeptide", "isolated peptide" and "isolated oligopeptide" refer to a protein (or respectively to a polypeptide, peptide, or oligopeptide) that is nonidentical to any protein molecule of identical amino acid sequence as found in nature; "isolated" does not require, although it does not prohibit, that the protein so described has itself been physically removed from its native environment. For example, a protein can be said to be "isolated" when it includes amino acid analogues or derivatives not found in nature, or includes linkages other than standard peptide bonds. When instead composed entirely of natural amino acids linked by peptide bonds, a protein can be said to be "isolated" when it exists at a purity not found in nature—where purity can be adjudged with respect to the presence of proteins of other sequence, with respect to the presence of non-protein compounds, such as nucleic acids, lipids, or other components of a biological cell, or when it exists in a composition not found in nature, such as in a host cell that does not naturally express that protein.

As used herein, a "purified polypeptide" (equally, a purified protein, peptide, or oligopeptide) represents at least 10% of the total protein present in a sample or preparation, as measured on a weight basis with respect to total protein in a composition. In preferred embodiments, the purified polypeptide represents at least about 50%, at least about 75%, or at least about 95% of the total protein in a sample or preparation. A "substantially purified protein" (equally, a substantially purified polypeptide, peptide, or oligopeptide) is an isolated protein, as above described, present at a concentration of at least 70%, as measured on a weight basis with respect to total protein in a composition. Reference to "purified polypeptide" does not require that the polypeptide has undergone any purification and may include, for example, chemically synthesized polypeptide that has not been purified.

As used herein, the term "antibody" refers to a polypeptide, at least a portion of which is encoded by at least one immunoglobulin gene, or fragment thereof, and that can bind specifically to a desired target molecule. The term includes naturally-occurring forms, as well as fragments and derivatives. Fragments within the scope of the term "antibody" include those produced by digestion with various proteases, those produced by chemical cleavage and/or chemical dissociation, and those produced recombinantly, so long as the fragment remains capable of specific binding to a target molecule. Among such fragments are Fab, Fab', Fv, F(ab)'$_2$, and single chain Fv (scFv) fragments. Derivatives within the scope of the term include antibodies (or fragments thereof) that have been modified in sequence, but remain capable of specific binding to a target molecule, including: interspecies chimeric and humanized antibodies; antibody fusions; heteromeric antibody complexes and antibody fusions, such as diabodies (bispecific antibodies), single-chain diabodies, and intrabodies (see, e.g., Marasco (ed.), *Intracellular Antibodies: Research and Disease Applications*, Springer-Verlag New York, Inc. (1998) (ISBN: 3540641513). As used herein, antibodies can be produced by any known technique, including harvest from cell culture of native B lymphocytes, harvest from culture of hybridomas, recombinant expression systems, and phage display.

As used herein, a "purified antibody preparation" is a preparation where at least 10% of the antibodies present bind to the target ligand. In preferred embodiments, antibodies binding to the target ligand represent at least about 50%, at least about 75%, or at least about 95% of the total antibodies present. Reference to "purified antibody preparation" does not require that the antibodies in the preparation have undergone any purification.

As used herein, "specific binding" refers to the ability of two molecular species concurrently present in a heterogeneous (inhomogeneous) sample to bind to one another in preference to binding to other molecular species in the sample. Typically, a specific binding interaction will discriminate over adventitious binding interactions in the reaction by at least two-fold, more typically by at least 10-fold, often at least 100-fold; when used to detect analyte, specific binding is sufficiently discriminatory when determinative of the presence of the analyte in a heterogeneous (inhomogeneous) sample. Typically, the affinity or avidity of a specific binding reaction is least about 1 µM.

The term "antisense", as used herein, refers to a nucleic acid molecule sufficiently complementary in sequence, and sufficiently long in that complementary sequence, as to hybridize under intracellular conditions to (i) a target mRNA transcript or (ii) the genomic DNA strand complementary to that transcribed to produce the target mRNA transcript.

The term "subject", as used herein refers to an organism and to cells or tissues derived therefrom. For example the organism may be an animal, including but not limited to animals such as cows, pigs, horses, chickens, cats, dogs, etc., and is usually a mammal, and most commonly human.

DETAILED DESCRIPTION OF THE INVENTION

This section presents a detailed description of the present invention and its applications. This description is by way of several exemplary illustrations, in increasing detail and specificity, of the general methods of this invention. These examples are non-limiting, and related variants that will be apparent to one of skill in the art are intended to be encompassed by the appended claims.

The present invention relates to the nucleic acid sequences encoding human ACC2sv1, that is an alternatively spliced isoform of ACC2, and to the amino acid sequences encoding this protein. SEQ ID NO 3 is a polynucleotide sequence representing an exemplary open reading frame that encodes the ACC2sv1 protein. SEQ ID NO 4 shows the polypeptide sequence of ACC2sv1.

ACC2sv1 polynucleotide sequence encoding ACC2sv1 protein, as exemplified and enabled herein include a number of specific, substantial and credible utilities. For example, ACC2sv1 encoding nucleic acids were identified in an mRNA sample obtained from a human source (see Example 1). Such nucleic acids can be used as hybridization probes to distinguish between cells that produce ACC2sv1 transcripts from human or non-human cells (including bacteria) that do not produce such transcripts. Similarly, antibodies specific for ACC2sv1 can be used to distinguish between cells that express ACC2sv1 from human or non-human cells (including bacteria) that do not express ACC2sv1.

The importance of ACC2 as a drug target for metabolic disorders including type II diabetes and obesity, or other metabolic syndrome-associated phenomena, is evidenced by the association of these diseases with fatty acid metabolism abnormalities (reviewed in Moller, 2001, Nature 414:821–827; Ruderman and Prentki, 2004, Nat. Rev. Drug. Discov. 3:340–351). Given the potential importance of ACC activity to the therapeutic management of features of metabolic syndrome, it is of value to identify ACC isoforms and identify ACC-ligand compounds that are isoform specific, as well as compounds that are effective ligands for two or more different ACC isoforms. In particular, it may be important to identify compounds that are effective inhibitors of a specific ACC isoform activity, yet do not bind to or interact with a plurality of different ACC isoforms. Compounds that bind to or interact with multiple ACC isoforms may require higher drug doses to saturate multiple ACC-isoform binding sites and thereby result in a greater likelihood of secondary non-therapeutic side effects. Furthermore, biological effects could also be caused by the interaction of a drug with the ACC2sv1 isoform specifically. For the foregoing reasons, ACC2sv1 protein represents a useful compound binding target and has utility in the identification of new ACC-ligands exhibiting a preferred specificity profile and having greater efficacy for their intended use.

In some embodiments, ACC2sv1 activity is modulated by a ligand compound to achieve one or more of the following: prevent or reduce the risk of occurrence, or recurrence of metabolic disorders including obesity, diabetes, and atherosclerosis.

Compounds modulating ACC2sv1 include agonists, antagonists, and allosteric modulators. Inhibitors of ACC2 achieve clinical efficacy by a number of known and unknown mechanisms. While not wishing to be limited to any particular theory of therapeutic efficacy, generally, but not always, ACC2sv1 compounds will be used to modulate the carboxylation of acetyl-CoA to malonyl-CoA. CP-610431 and its more stable analog, CP-640186 act as inhibitors of malonyl-CoA production (Harwood et al., 2003, J. Biol. Chem. 278:37099–37111). ESP 55016, when converted to ESP 55016-CoA, directly inhibits ACC activity (Cramer et al., Apr. 21, 2004, J. Lipid Res. Epub ahead of print). Therefore, agents that modulate ACC2 activity may be used to achieve a therapeutic benefit for any disease or condition due to, or exacerbated by, ACC2 activity.

ACC2sv1 activity can also be affected by modulating the cellular abundance of transcripts encoding ACC2sv1. Compounds modulating the abundance of transcripts encoding ACC2sv1 include a cloned polynucleotide encoding ACC2sv1, that can express ACC2sv1 in vivo, antisense nucleic acids targeted to ACC2sv1 transcripts, enzymatic nucleic acids, such as ribozymes, and RNAi nucleic acids, such as shRNAs or siRNAs, targeted to ACC2sv1 transcripts.

In some embodiments, ACC2sv1 activity is modulated to achieve a therapeutic effect upon diseases in which regulation of ACC2 is desirable. For example, metabolic disorders such as obesity and type II diabetes may be treated by modulating ACC2sv1 activity.

ACC2sv1 Nucleic Acids

ACC2sv1 nucleic acids contain regions that encode for polypeptides comprising, consisting, or consisting essentially of SEQ ID NO 4. The ACC2sv1 nucleic acids have a variety of uses, such as use as a hybridization probe or PCR primer to identify the presence of ACC2sv1; use as a hybridization probe or PCR primer to identify nucleic acids encoding for proteins related to ACC2sv1; and/or use for recombinant expression of ACC2sv1. In particular, ACC2sv1 polynucleotides have replaced the polynucleotide region that consists of exon 1 of the ACC2 gene with an alternative exon 1A (SEQ ID NO 2).

Regions in ACC2sv1 nucleic acid that do not encode for ACC2sv1, or are not found in SEQ ID NO 3, if present, are preferably chosen to achieve a particular purpose. Examples of additional regions that can be used to achieve a particular purpose include: a stop codon that is effective at protein synthesis termination; capture regions that can be used as part of an ELISA sandwich assay; reporter regions that can be probed to indicate the presence of the nucleic acid; expression vector regions; and regions encoding for other polypeptides.

The guidance provided in the present application can be used to obtain the nucleic acid sequence encoding ACC2sv1 related proteins from different sources. Obtaining nucleic acids encoding ACC2sv1 related proteins from different sources is facilitated by using sets of degenerative probes and primers and the proper selection of hybridization conditions. Sets of degenerative probes and primers are produced taking into account the degeneracy of the genetic code. Adjusting hybridization conditions is useful for controlling probe or primer specificity to allow for hybridization to nucleic acids having similar sequences.

Techniques employed for hybridization detection and PCR cloning are well known in the art. Nucleic acid detection techniques are described, for example, in Sambrook, et al., in *Molecular Cloning, A Laboratory Manual*, $2^{nd}$ Edition, Cold Spring Harbor Laboratory Press, 1989. PCR cloning techniques are described, for example, in White, *Methods in Molecular Cloning*, volume 67, Humana Press, 1997.

ACC2sv1 probes and primers can be used to screen nucleic acid libraries containing, for example, cDNA. Such libraries are commercially available, and can be produced using techniques such as those described in Ausubel, *Current Protocols in Molecular Biology*, John Wiley, 1987–1998.

Starting with a particular amino acid sequence and the known degeneracy of the genetic code, a large number of different encoding nucleic acid sequences can be obtained. The degeneracy of the genetic code arises because almost all amino acids are encoded for by different combinations of nucleotide triplets or "codons". The translation of a particular codon into a particular amino acid is well known in the art (see, e.g., Lewin *GENES IV*, p. 119, Oxford University Press, 1990). Amino acids are encoded for by codons as follows:

A=Ala=Alanine: codons GCA, GCC, GCG, GCU
C=Cys=Cysteine: codons UGC, UGU
D=Asp=Aspartic acid: codons GAC, GAU
E=Glu=Glutamic acid: codons GAA, GAG
F=Phe=Phenylalanine: codons UUC, UUU
G=Gly=Glycine: codons GGA, GGC, GGG, GGU
H=His=Histidine: codons CAC, CAU
I=Ile=Isoleucine: codons AUA, AUC, AUU
K=Lys=Lysine: codons AAA, AAG
L=Leu=Leucine: codons UUA, UUG, CUA, CUC, CUG, CUU
M=Met=Methionine: codon AUG
N=Asn=Asparagine: codons AAC, AAU
P=Pro=Proline: codons CCA, CCC, CCG, CCU
Q=Gln=Glutamine: codons CAA, CAG
R=Arg=Arginine: codons AGA, AGG, CGA, CGC, CGG, CGU
S=Ser=Serine: codons AGC, AGU, UCA, UCC, UCG, UCU
T=Thr=Threonine: codons ACA, ACC, ACG, ACU
V=Val=Valine: codons GUA, GUC, GUG, GUU
W=Trp=Tryptophan: codon UGG
Y=Tyr=Tyrosine: codons UAC, UAU Nucleic acid having a desired sequence can be synthesized using chemical and biochemical techniques. Examples of chemical techniques are described in Ausubel, *Current Protocols in Molecular Biology*, John Wiley, 1987–1998, and Sambrook et al., in *Molecular Cloning, A Laboratory Manual*, $2^{nd}$ Edition, Cold Spring Harbor Laboratory Press, 1989. In addition, long polynucleotides of a specified nucleotide sequence can be ordered from commercial vendors, such as Blue Heron Biotechnology, Inc. (Bothell, Wash.).

Biochemical synthesis techniques involve the use of a nucleic acid template and appropriate enzymes such as DNA and/or RNA polymerases. Examples of such techniques include in vitro amplification techniques such as PCR and transcription based amplification, and in vivo nucleic acid replication. Examples of suitable techniques are provided by Ausubel, *Current Protocols in Molecular Biology*, John Wiley, 1987–1998, Sambrook et al., in *Molecular Cloning, A Laboratory Manual*, 2$^{nd}$ Edition, Cold Spring Harbor Laboratory Press, 1989, and U.S. Pat. No. 5,480,784.

ACC2sv1 Probes

Probes for ACC2sv1 contain a region that can specifically hybridize to ACC2sv1 target nucleic acids, under appropriate hybridization conditions and can distinguish ACC2sv1 nucleic acids from each other and from non-target nucleic acids, in particular ACC2 polynucleotides not containing exon 1A. Probes for ACC2sv1 can also contain nucleic acid regions that are not complementary to ACC2sv1 nucleic acids.

In embodiments where, for example, ACC2sv1 polynucleotide probes are used in hybridization assays to specifically detect the presence of ACC2sv1 polynucleotides in samples, the ACC2sv1 polynucleotides comprise at least 20 nucleotides of the ACC2sv1 sequence that correspond to the respective novel exon junction or novel polynucleotide regions. In particular, for detection of ACC2sv1, the probe comprises at least 20 nucleotides of the ACC2sv1 sequence that corresponds to an exon junction polynucleotide created by the alternative splicing of exon 1A to exon 2 of the primary transcript of the ACC2 gene (see FIGS. 1A and 1B). For example, the polynucleotide sequence: 5' GCGAAGTAAAGCCGAGCATG 3' (SEQ ID NO 5) represents one embodiment of such an inventive ACC2sv1 polynucleotide wherein a first 10 nucleotide region is complementary and hybridizable to the 3' end of exon 1A of the ACC2sv1 gene and a second 10 nucleotide region is complementary and hybridizable to the 5' end of exon 2 of the ACC2sv1 gene (see FIG. 1B).

In some embodiments, the first 20 nucleotides of an ACC2sv1 probe comprise a first continuous region of 5 to 15 nucleotides that is complementary and hybridizable to the 3' end of exon 1A and a second continuous region of 5 to 15 nucleotides that is complementary and hybridizable to the 5' end of exon 2.

In other embodiments, the ACC2sv1 polynucleotide comprises at least 40, 60, 80 or 100 nucleotides of the ACC2sv1 sequence, that correspond to a junction polynucleotide region created by the alternative splicing of exon 1A to exon 2 in the case of ACC2sv1. The ACC2sv1 polynucleotide is selected to comprise a first continuous region of at least 5 to 15 nucleotides that is complementary and hybridizable to the 3' end of exon 1A and a second continuous region of at least 5 to 15 nucleotides that is complementary and hybridizable to the 5' end of exon 2. A large number of different polynucleotide sequences from the region of the exon 1A to exon 2 splice junction may be selected which will, under appropriate hybridization conditions, have the capacity to detectably hybridize to ACC2sv1 polynucleotide and yet will hybridize to a much less extent or not at all to ACC2 isoform polynucleotides wherein exon IA is not spliced to exon 2.

Preferably, non-complementary nucleic acid that is present has a particular purpose such as being a reporter sequence or being a capture sequence. However, additional nucleic acid need not have a particular purpose as long as the additional nucleic acid does not prevent the ACC2sv1 nucleic acid from distinguishing between target polynucleotides, e.g., ACC2sv1 polynucleotides, and non-target polynucleotides, including, but not limited to ACC2 polynucleotides not comprising the exon 1A, to exon 2 splice junction found in ACC2sv1.

Hybridization occurs through complementary nucleotide bases. Hybridization conditions determine whether two molecules, or regions, have sufficiently strong interactions with each other to form a stable hybrid.

The degree of interaction between two molecules that hybridize together is reflected by the melting temperature ($T_m$) of the produced hybrid. The higher the $T_m$ the stronger the interactions and the more stable the hybrid. $T_m$ is effected by different factors well known in the art such as the degree of complementarity, the type of complementary bases present (e.g., A-T hybridization versus G-C hybridization), the presence of modified nucleic acid, and solution components (e.g., Sambrook, et al., in *Molecular Cloning, A Laboratory Manual*, 2$^{nd}$ Edition, Cold Spring Harbor Laboratory Press, 1989).

Stable hybrids are formed when the $T_m$ of a hybrid is greater than the temperature employed under a particular set of hybridization assay conditions. The degree of specificity of a probe can be varied by adjusting the hybridization stringency conditions. Detecting probe hybridization is facilitated through the use of a detectable label. Examples of detectable labels include luminescent, enzymatic, and radioactive labels.

Examples of stringency conditions are provided in Sambrook, et al., in *Molecular Cloning, A Laboratory Manual*, 2$^{nd}$ Edition, Cold Spring Harbor Laboratory Press, 1989. An example of high stringency conditions is as follows: Prehybridization of filters containing DNA is carried out for 2 hours to overnight at 65° C. in buffer composed of 6×SSC, 5× Denhardt's solution, and 100 µg/ml denatured salmon sperm DNA. Filters are hybridized for 12 to 48 hours at 65° C. in prehybridization mixture containing 100 µg/ml denatured salmon sperm DNA and 5–20×10$^6$ cpm of $^{32}$P-labeled probe. Filter washing is done at 37° C. for 1 hour in a solution containing 2×SSC, 0.1% SDS. This is followed by a wash in 0.1×SSC, 0.1% SDS at 50° C. for 45 minutes before autoradiography. Other procedures using conditions of high stringency would include, for example, either a hybridization step carried out in 5× SSC, 5× Denhardt's solution, 50% formamide at 42° C. for 12 to 48 hours or a washing step carried out in 0.2×SSPE, 0.2% SDS at 65° C. for 30 to 60 minutes.

Recombinant Expression

ACC2sv1 polynucleotides, such as those comprising SEQ ID NO 3, can be used to make ACC2sv1 polypeptides. In particular, ACC2sv1 polypeptides can be expressed from recombinant nucleic acids in a suitable host or in vitro using a translation system. Recombinantly expressed ACC2sv1 polypeptides can be used, for example, in assays to screen for compounds that bind ACC2sv1. Alternatively, ACC2sv1 polypeptides can also be used to screen for compounds that bind to one or more ACC isoforms, but do not bind to ACC2sv1.

In some embodiments, expression is achieved in a host cell using an expression vector. An expression vector contains recombinant nucleic acid encoding a polypeptide along with regulatory elements for proper transcription and processing. The regulatory elements that may be present include those naturally associated with the recombinant nucleic acid and exogenous regulatory elements not naturally associated with the recombinant nucleic acid. Exogenous regulatory elements such as an exogenous promoter can be useful for expressing recombinant nucleic acid in a particular host.

Generally, the regulatory elements that are present in an expression vector include a transcriptional promoter, a ribosome binding site, a terminator, and an optionally present operator. Another preferred element is a polyadenylation signal providing for processing in eukaryotic cells. Preferably, an expression vector also contains an origin of replication for autonomous replication in a host cell, a selectable marker, a limited number of useful restriction enzyme sites, and a potential for high copy number. Examples of expression vectors are cloning vectors, modified cloning vectors, and specifically designed plasmids and viruses.

Expression vectors providing suitable levels of polypeptide expression in different hosts are well known in the art. Mammalian expression vectors well known in the art include, but are not restricted to, pcDNA3 (Invitrogen, Carlsbad Calif.), pSecTag2 (Invitrogen), pMClneo (Stratagene, La Jolla Calif.), pXT1 (Stratagene), pSG5 (Stratagene), pCMVLacl (Stratagene), pCI-neo (Promega), EBO-pSV2-neo (ATCC 37593), pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146) and pUCTag (ATCC 37460). Bacterial expression vectors well known in the art include pET11a (Novagen), pBluescript SK (Stratagene, La Jolla), pQE-9 (Qiagen Inc., Valencia), lambda gt11 (Invitrogen), pcDNAII (Invitrogen), and pKK223–3 (Pharmacia). Fungal cell expression vectors well known in the art include pRS416 (ATCC 87521), pPICZ (Invitrogen), pYES2 (Invitrogen), and Pichia expression vector (Invitrogen). Insect cell expression vectors well known in the art include Blue Bac III (Invitrogen), pBacPAK8 (CLONTECH, Inc., Palo Alto) and PfastBacHT (Invitrogen, Carlsbad, Calif.).

Recombinant host cells may be prokaryotic or eukaryotic. Examples of recombinant host cells include the following: bacteria such as *E. coli*; fungal cells such as yeast; mammalian cells such as human, bovine, porcine, monkey and rodent; and insect cells such as *Drosophila* and silkworm derived cell lines. Commercially available mammalian cell lines include L cells L-M(TK$^-$) (ATCC CCL 1.3), L cells L-M (ATCC CCL 1.2), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26) MRC-5 (ATCC CCL 171), and HEK 293 cells (ATCC CRL-1573).

To enhance expression in a particular host it may be useful to modify the sequence provided in SEQ ID NO 3 to take into account codon usage of the host. Codon usages of different organisms are well known in the art (see, Ausubel, *Current Protocols in Molecular Biology*, John Wiley, 1987–1998, Supplement 33 Appendix 1C).

Expression vectors may be introduced into host cells using standard techniques. Examples of such techniques include transformation, transfection, lipofection, protoplast fusion, and electroporation.

Nucleic acids encoding for a polypeptide can be expressed in a cell without the use of an expression vector employing, for example, synthetic mRNA or native mRNA. Additionally, mRNA can be translated in various cell-free systems such as wheat germ extracts and reticulocyte extracts, as well as in cell based systems, such as frog oocytes. Introduction of mRNA into cell based systems can be achieved, for example, by microinjection or electroporation.

ACC2sv1 Polypeptides

ACC2sv1 polypeptides contain an amino acid sequence comprising, consisting or consisting essentially of SEQ ID NO 4. ACC2sv1 polypeptides have a variety of uses, such as providing a marker for the presence of ACC2sv1; use as an immunogen to produce antibodies binding to ACC2sv1; use as a target to identify compounds binding selectively to ACC2sv1; or use in an assay to identify compounds that bind to one or more ACC isoforms but do not bind to or interact with ACC2sv1.

In chimeric polypeptides containing one or more regions from ACC2sv1 and one or more regions not from ACC2sv1, the region(s) not from ACC2sv1 can be used, for example, to achieve a particular purpose or to produce a polypeptide that can substitute for ACC2sv1, or fragments thereof. Particular purposes that can be achieved using chimeric ACC2sv1 polypeptides include providing a marker for ACC2sv1 activity, enhancing an immune response, and altering the activity and regulation of ACC2.

Polypeptides can be produced using standard techniques including those involving chemical synthesis and those involving biochemical synthesis. Techniques for chemical synthesis of polypeptides are well known in the art (see e.g., Vincent, in *Peptide and Protein Drug Delivery*, New York, N.Y., Dekker, 1990).

Biochemical synthesis techniques for polypeptides are also known in the art. Such techniques employ a nucleic acid template for polypeptide synthesis. The genetic code providing the sequences of nucleic acid triplets coding for particular amino acids is well known in the art (see, e.g., Lewin *GENES IV*, p. 119, Oxford University Press, 1990). Examples of techniques for introducing nucleic acid into a cell and expressing the nucleic acid to produce protein are provided in references such as Ausubel, *Current Protocols in Molecular Biology*, John Wiley, 1987–1998, and Sambrook, et al., in *Molecular Cloning, A Laboratory Manual*, $2^{nd}$ Edition, Cold Spring Harbor Laboratory Press, 1989.

Functional ACC2sv1

Functional ACC2sv1 is a different protein isoform of ACC2. The identification of the amino acid and nucleic acid sequences of ACC2sv1 provides tools for obtaining functional proteins related to ACC2sv1 from other sources, for producing ACC2sv1 chimeric proteins, and for producing functional derivatives of SEQ ID NO 4.

ACC2sv1 polypeptides can be readily identified and obtained based on their sequence similarity to ACC2sv1 (SEQ ID NO 4). In particular, ACC2sv1 lacks the amino acids encoded by exon 1 of the ACC2 gene and retains a 261 base pair alternative exon 1A (SEQ ID NO 2) deriving from the sequence of intron 1. The ACC2sv1 polypeptide also initiates at an alternative start codon in exon 1A, located 47 nucleotides from the end of exon 1A. The replacement of exon 1 with exon 1A and the use of alternative start codon in exon 1A do not alter the protein translation reading frame as compared to the ACC2 reference sequence (AJ575592). Thus, the ACC2sv1 polypeptide is lacking the amino acids encoded by the nucleotides corresponding to exon 1 of the ACC2 reference transcript (AJ575592) and possesses a unique N-terminal 16 amino acid region encoded by the nucleotides corresponding to exon 1A.

Both the amino acid and nucleic acid sequences of ACC2sv1 can be used to help identify and obtain ACC2sv1 polypeptides. For example, SEQ ID NO 3 can be used to produce degenerative nucleic acid probes or primers for identifying and cloning nucleic acid polynucleotides encoding for an ACC2sv1 polypeptide. In addition, polynucleotides comprising, consisting, or consisting essentially of SEQ ID NO 3 or fragments thereof, can be used under conditions of moderate stringency to identify and clone nucleic acids encoding ACC2sv1 polypeptides from a variety of different organisms.

The use of degenerative probes and moderate stringency conditions for cloning is well known in the art. Examples of such techniques are described by Ausubel, *Current Protocols in Molecular Biology*, John Wiley, 1987–1998, and Sambrook, et al., in *Molecular Cloning, A Laboratory Manual*, $2^{nd}$ Edition, Cold Spring Harbor Laboratory Press, 1989.

Starting with ACC2sv1 obtained from a particular source, derivatives can be produced. Such derivatives include polypeptides with amino acid substitutions, additions and deletions. Changes to ACC2sv1 to produce a derivative having essentially the same properties should be made in a manner not altering the tertiary structure of ACC2sv1.

Differences in naturally occurring amino acids are due to different R groups. An R group affects different properties of the amino acid such as physical size, charge, and hydrophobicity. Amino acids are can be divided into different groups as follows: neutral and hydrophobic (alanine, valine, leucine, isoleucine, proline, tryptophan, phenylalanine, and methionine); neutral and polar (glycine, serine, threonine, tryosine, cysteine, asparagine, and glutamine); basic (lysine, arginine, and histidine); and acidic (aspartic acid and glutamic acid).

Generally, in substituting different amino acids it is preferable to exchange amino acids having similar properties. Substituting different amino acids within a particular group, such as substituting valine for leucine, arginine for lysine, and asparagine for glutamine are good candidates for not causing a change in polypeptide functioning.

Changes outside of different amino acid groups can also be made. Preferably, such changes are made taking into account the position of the amino acid to be substituted in the polypeptide. For example, arginine can substitute more freely for nonpolar amino acids in the interior of a polypeptide then glutamate because of its long aliphatic side chain (See, Ausubel, *Current Protocols in Molecular Biology*, John Wiley, 1987–1998, Supplement 33 Appendix 1C).

ACC2sv1 Antibodies

Antibodies recognizing ACC2sv1 can be produced using a polypeptide containing SEQ ID NO 4, or a fragment thereof as an immunogen. Preferably, an ACC2sv1 polypeptide used as an immunogen consists of a polypeptide of SEQ ID NO 4 or a SEQ ID NO 4 fragment having at least 10 contiguous amino acids in length corresponding to the polynucleotide region representing the junction resulting from the splicing of exon 1A to exon 2 of the ACC2 gene.

In some embodiments where, for example, ACC2sv1 polypeptides are used to develop antibodies that bind specifically to ACC2sv1 and not to other isoforms of ACC, the ACC2sv1 polypeptides comprise at least 10 amino acids of the ACC2sv1 polypeptide sequence corresponding to a junction polynucleotide region created by the alternative splicing of exon 1A to exon 2 of the primary transcript of the ACC2 gene (see FIG. 1). For example, the amino acid sequence: amino terminus-DREVKPSMSG-carboxy terminus (SEQ ID NO 6) represents one embodiment of such an inventive ACC2sv1 polypeptide wherein a first 5 amino acid region is encoded by a nucleotide sequence at the 3' end of exon 1A of the ACC2 gene and a second 5 amino acid region is encoded by the nucleotide sequence directly after the novel splice junction. Preferably, at least 10 amino acids of the ACC2sv1 polypeptide comprise a first continuous region of 2 to 8 amino acids that is encoded by nucleotides at the 3' end of exon 1A and a second continuous region of 2 to 8 amino acids that is encoded by nucleotides at the 5' end of exon 2.

In other embodiments, ACC2sv1-specific antibodies are made using an ACC2sv1 polypeptide that comprises at least 20, 30, 40 or 50 amino acids of the ACC2sv1 sequence that corresponds to a junction polynucleotide region created by the alternative splicing of exon 1A to exon 2 of the primary transcript of the ACC2 gene. In each case the ACC2sv1 polypeptides are selected to comprise a first continuous region of at least 5 to 15 amino acids that is encoded by nucleotides at the 3' end of exon 1A and a second continuous region of 5 to 15 amino acids that is encoded by nucleotides directly after the novel splice junction.

Antibodies to ACC2sv1 have different uses, such as to identify the presence of ACC2sv1, and to isolate ACC2sv1 polypeptides. Identifying the presence of ACC2sv1 can be used, for example, to identify cells producing ACC2sv1. Such identification provides an additional source of ACC2sv1 and can be used to distinguish cells known to produce ACC2sv1 from cells that do not produce ACC2sv1. For example, antibodies to ACC2sv1 can distinguish human cells expressing ACC2sv1 from human cells not expressing ACC2sv1 or non-human cells (including bacteria) that do not express ACC2sv1. Such ACC2sv1 antibodies can also be used to determine the effectiveness of ACC2sv1 ligands, using techniques well known in the art, to detect and quantify changes in the protein levels of ACC2sv1 in cellular extracts, and in situ immunostaining of cells and tissues.

Techniques for producing and using antibodies are well known in the art. Examples of such techniques are described in Ausubel, *Current Protocols in Molecular Biology*, John Wiley, 1987–1998; Harlow, et al., *Antibodies, A Laboratory Manual*, Cold Spring Harbor Laboratory, 1988; and Kohler, et al., 1975 Nature 256:495–7.

ACC2sv1 Binding Assay

A number of compounds known to modulate ACC2 activity have been disclosed. CP-610431, CP-640186, and ESP 55016-CoA act as inhibitors of ACC2 function (Harwood et al., 2003, J. Biol. Chem. 278:37099–37111; Cramer et al., Apr. 21, 2004, J. Lipid Res. Epub ahead of print). Derivatives of soraphen, an anti-fungal agent, have been found to be potent ACC inhibitors (U.S. Patent Application 2003/0144345). Additional ACC inhibitors have also been disclosed (U.S. Pat. No. 6,485,941 and U.S. Patent Application 2003/0187254). Methods for monitoring the activity of ACC, including analyzing the effect of compounds on the activity of ACC activity, have been described previously (U.S. patent Application No. 2003/0187254 and International Publication Number WO 2004/013159). Methods for screening compounds for their effects on ACC2 activity have also been described (see for example, International Publication Number WO 02/079501). A person skilled in the art should be able to use these methods to screen ACC2sv1 polypeptide for compounds that bind to, and in some cases functionally alter, ACC isoform proteins.

ACC2sv1 or fragments thereof, can be used in binding studies to identify compounds binding to or interacting with ACC2sv1, or fragments thereof. In one embodiment, ACC2sv1, or a fragment thereof, can be used in binding studies with an ACC isoform protein, or a fragment thereof, to identify compounds that: bind to or interact with ACC2sv1 and other ACC isoforms; bind to or interact with one or more other ACC isoforms and not with ACC2sv1; bind to or interact with ACC2sv1 and not with one or more other ACC isoforms. Such binding studies can be performed using different formats including competitive and non-competitive formats. Further competition studies can be carried out using additional compounds determined to bind to ACC2sv1 or other ACC1 or ACC2 isoforms.

The particular ACC2sv1 sequence involved in ligand binding can be identified using labeled compounds that bind to the protein and different protein fragments. Different strategies can be employed to select fragments to be tested to narrow down the binding region. Examples of such strategies include testing consecutive fragments about 15 amino acids in length starting at the N-terminus, and testing longer length fragments. If longer length fragments are tested, a fragment binding to a compound can be subdivided to further locate the binding region. Fragments used for binding studies can be generated using recombinant nucleic acid techniques.

In some embodiments, binding studies are performed using ACC2sv1 expressed from a recombinant nucleic acid. Alternatively, recombinantly expressed ACC2sv1 consists of the SEQ ID NO 4 amino acid sequence.

Binding assays can be performed using individual compounds or preparations containing different numbers of compounds. A preparation containing different numbers of compounds having the ability to bind to ACC2sv1 can be divided into smaller groups of compounds that can be tested to identify the compound(s) binding to ACC2sv1.

Binding assays can be performed using recombinantly produced ACC2sv1 present in different environments. Such environments include, for example, cell extracts and purified cell extracts containing an ACC2sv1 recombinant nucleic acid; and also include, for example, the use of a purified ACC2sv1 polypeptide produced by recombinant means which is introduced into different environments.

In one embodiment of the invention, a binding method is provided for screening for a compound able to bind selectively to ACC2sv1. The method comprises the steps: providing a ACC2sv1 polypeptide comprising SEQ ID NO 4; providing an ACC isoform polypeptide that is not ACC2sv1; contacting the ACC2sv1 polypeptide and the ACC isoform polypeptide that is not ACC2sv1 with a test preparation comprising one or more test compounds; and then determining the binding of the test preparation to the ACC2sv1 polypeptide and to the ACC isoform polypeptide that is not ACC2sv1, wherein a test preparation that binds to the ACC2sv1 polypeptide, but does not bind to the ACC isoform polypeptide that is not ACC2sv1, contains one or more compounds that selectively bind to ACC2sv1.

In another embodiment of the invention, a binding method is provided for screening for a compound able to bind selectively to an ACC isoform polypeptide that is not ACC2sv1. The method comprises the steps: providing a ACC2sv1 polypeptide comprising SEQ ID NO 4; providing an ACC isoform polypeptide that is not ACC2sv1; contacting the ACC2sv1 polypeptide and the ACC isoform polypeptide that is not ACC2sv1 with a test preparation comprising one or more test compounds; and then determining the binding of the test preparation to the ACC2sv1 polypeptide and the ACC isoform polypeptide that is not ACC2sv1, wherein a test preparation that binds the ACC isoform polypeptide that is not ACC2sv1, but does not bind ACC2sv1, contains a compound that selectively binds the ACC isoform polypeptide that is not ACC2sv1.

The above-described selective binding assays can also be performed with a polypeptide fragment of ACC2sv1, wherein the polypeptide fragment comprises at least 10 consecutive amino acids that are coded by a nucleotide sequence that bridges the junction created by the splicing of the 3' end of exon 1A to the 5' end of exon 2 in the case of ACC2sv1. Similarly, the selective binding assays may also be performed using a polypeptide fragment of a ACC2 isoform polypeptide that is not ACC2sv1, wherein the polypeptide fragment comprises at least 10 consecutive amino acids that are coded by: a) a nucleotide sequence that is contained within exon 1 of the ACC2 gene or b) a nucleotide sequence that bridges the junction created by the splicing of the 3' end of exon 1 to the 5' end of exon 2 of the ACC2 gene.

ACC Functional Assays

ACC2 encodes acetyl coenzyme A carboxylase 2, an important component of fatty acid metabolism pathways, inhibiting fatty acid oxidation with its product malonyl-CoA in response to nutritional, hormonal, and cellular stress signals. The identification of ACC2sv1 as a splice variant of ACC2 provides a means of screening for compounds that bind to ACC2sv1 protein thereby altering the activity or regulation of ACC2sv1. Assays involving a functional ACC2sv1 polypeptide can be employed for different purposes, such as selecting for compounds active at ACC2sv1; evaluating the ability of a compound to affect the activity of each respective splice variant; and mapping the activity of different ACC2sv1 regions. ACC2sv1 activity can be measured using different techniques such as: detecting a change in the intracellular conformation of ACC2sv1; detecting a change in the intracellular location of ACC2sv1; or measuring the carboxylase activity of ACC2sv1.

Recombinantly expressed ACC2sv1 can be used to facilitate the determination of whether a compound's activity in a cell is dependent upon the presence of ACC2sv1. For example, ACC2sv1 can be expressed by an expression vector in a cell line and used in a co-culture growth assay, such as described in U.S. Pat. No. 6,518,035, to identify compounds that alter the growth of the cell expressing ACC2sv1 from the expression vector as compared to the same cell line but lacking the ACC2sv1 expression vector. Alternatively, determination of whether a compound's activity on a cell is dependent upon the presence of ACC2sv1 can also be done using gene expression profile analysis methods as described, for example, in U.S. Pat. No. 6,324,479.

Methods to determine ACC activity are known in the art. A radiochemical method that measures incorporation of [$^{14}$C] bicarbonate into [$^{14}$C] malonyl-CoA and separates products from unused substrate at the reaction's end by acidification has been described (Harwood et al., 2003, J. Biol. Chem. 278:37099–37111; Vavvas et al., 1997, J. Biol. Chem. 272:13255–13261; International Publication WO 2004/013159). Acidification acts to quench the reaction and remove residual radiolabeled substrate as $^{14}CO_2$. Methods for expressing ACC2 in HEK293 cells and monitoring the activity of ACC2, including analyzing the effect of compounds on ACC2 activity, have been described previously (U.S. Patent Application 2003/0144345). High throughput methods for assaying ACC2 activity and inhibition have also been described (Harwood et al., 2003, J. Biol. Chem. 278:37099–37111). A variety of other assays has been used to investigate the properties of ACC1 and ACC2, and therefore, would also be applicable to the measurement of ACC2sv1.

ACC2sv1 functional assays can be performed using cells expressing ACC2sv1 at a high level. These proteins will be contacted with individual compounds or preparations containing different compounds. A preparation containing different compounds where one or more compounds affect ACC2sv1 in cells over-producing ACC2sv1 as compared to control cells containing an expression vector lacking ACC2sv1 coding sequences, can be divided into smaller groups of compounds to identify the compound(s) affecting ACC2sv1 activity.

ACC2sv1 functional assays can be performed using recombinantly produced ACC2sv1 present in different environments. Such environments include, for example, cell extracts and purified cell extracts containing the ACC2sv1 expressed from recombinant nucleic acid; and the use of purified ACC2sv1 produced by recombinant means that is introduced into a different environment suitable for measuring ACC activity.

Modulating ACC2sv1 Expression

ACC2sv1 expression can be modulated as a means for increasing or decreasing ACC2sv1 activity. Such modulation includes inhibiting the activity of nucleic acids encoding the ACC2 isoform target to reduce ACC2 isoform protein or polypeptide expression, or supplying ACC2 nucleic acids to increase the level of expression of the ACC2 target polypeptide thereby increasing ACC2 activity.

Inhibition of ACC2sv1 Activity

ACC2sv1 nucleic acid activity can be inhibited using nucleic acids recognizing ACC2sv1 nucleic acid and affecting the ability of such nucleic acid to be transcribed or translated. Inhibition of ACC2sv1 nucleic acid activity can be used, for example, in target validation studies.

A preferred target for inhibiting ACC2sv1 is mRNA stability and translation. The ability of ACC2sv1 mRNA to be translated into a protein can be effected by compounds such as anti-sense nucleic acid, RNA interference (RNAi) and enzymatic nucleic acid.

Anti-sense nucleic acid can hybridize to a region of a target mRNA. Depending on the structure of the anti-sense nucleic acid, anti-sense activity can be brought about by different mechanisms such as blocking the initiation of translation, preventing processing of mRNA, hybrid arrest, and degradation of mRNA by RNAse H activity.

RNA inhibition (RNAi) using shRNA or siRNA molecules can also be used to prevent protein expression of a target transcript. This method is based on the interfering properties of double-stranded RNA derived from the coding region of a gene that disrupts the synthesis of protein from transcribed RNA.

Enzymatic nucleic acids can recognize and cleave other nucleic acid molecules. Preferred enzymatic nucleic acids are ribozymes.

General structures for anti-sense nucleic acids, RNAi and ribozymes, and methods of delivering such molecules, are well known in the art. Modified and unmodified nucleic acids can be used as anti-sense molecules, RNAi and ribozymes. Different types of modifications can affect certain RNA activities such as the ability to be cleaved by RNAse H, and can affect nucleic acid stability. Examples of references describing different anti-sense molecules, and ribozymes, and the use of such molecules, are provided in U.S. Pat. Nos. 5,849,902; 5,859,221; 5,852,188; and 5,616,459. Examples of organisms in which RNAi has been used to inhibit expression of a target gene include: *C. elegans* (Tabara, et al., 1999, Cell 99, 123–32; Fire, et al., 1998, Nature 391, 806–11), plants (Hamilton and Baulcombe, 1999, Science 286, 950–52), *Drosophila* (Hammond, et al., 2001, Science 293, 1146–50; Misquitta and Patterson, 1999, Proc. Nat. Acad. Sci. 96, 1451–56; Kennerdell and Carthew, 1998, Cell 95, 1017–26), and mammalian cells (Bernstein, et al., 2001, Nature 409, 363–6; Elbashir, et al., 2001, Nature 411, 494–8).

Increasing ACC2sv1 Expression

Nucleic acids encoding for ACC2sv1 can be used, for example, to cause an increase in ACC2 activity or to create a test system (e.g., a transgenic animal) for screening for compounds affecting ACC2sv1 expression, respectively. Nucleic acids can be introduced and expressed in cells present in different environments.

Guidelines for pharmaceutical administration in general are provided in, for example, *Remington's Pharmaceutical Sciences*, 18$^{th}$ Edition, supra, and *Modern Pharmaceutics*, 2$^{nd}$ Edition, supra Nucleic acid can be introduced into cells present in different environments using in vitro, in vivo, or ex vivo techniques. Examples of techniques useful in gene therapy are illustrated in *Gene Therapy & Molecular Biology: From Basic Mechanisms to Clinical Applications*, Ed. Boulikas, Gene Therapy Press, 1998.

EXAMPLES

Examples are provided below to further illustrate different features and advantages of the present invention. The examples also illustrate useful methodology for practicing the invention. These examples do not limit the claimed invention.

Example 1

Identification of ACC2sv1 Using Genomically Aligned ESTs and RT-PCR

Using computational and experimental methods, an alternatively spliced isoform of ACC2 was identified. Alternative splicing analysis of the ACC2 gene was performed by aligning expressed sequence tags (EST) to the genomic sequence. Methods for gene structure prediction using genomically aligned ESTs are known in the art and have been described (Mironov et al., 1999, Genome Res. 9:1288–1293; Kan et al., 2001, Genome Res. 11:889–900; Kan et al., 2002, Genome Res. 12:1837–1845; Modrek et al., 2001, Nucleic Acids Res. 29:2850–2859). The mRNA transcript sequence for ACC2 (AJ575592) and ACC2 EST sequences were aligned to the ACC2 genomic sequence using the sim4 alignment program (Florea et al., 1998; Genome Res. 8:967–974), which allows for introns in the genomic sequence and a small number of sequencing errors. The Transcript Assembly Program (TAP, Kan et al., 2001, Genome Res. 11:889–900) was used to predict the gene structure from the genomic EST alignment and compare the predicted gene structures with the known gene structures. Human EST (CA392208) and mouse EST (BB866065.1) were identified as containing a splicing pattern different from the ACC2 mRNA transcript AJ575592. Human EST (CA392208) and mouse EST (BB866065.1) contain an exon 1 not found in AJ575592 or any other known mRNA sequences. This novel ACC2 splice isoform was predicted to have used an alternative exon 1 (exon 1A), located within intron 1 of the ACC2 gene.

To test this computational prediction of a novel ACC2 splice isoform, the structure of ACC2 mRNA in the region corresponding to exon 1A to exon 5, which encompasses the unique N-terminal domain of ACC2, was determined for a panel of human tissues and cell line samples using an RT-PCR based assay. PolyA purified mRNA isolated from human adipose tissue, skeletal muscle, heart, liver, and testis was obtained from BD Biosciences Clontech (Palo Alto, Calif.). RT-PCR primers were selected that were complementary to sequences in exon 1A and exon 5 of the human EST (CA392208) and mouse EST (BB866065.1), and reference exon coding sequences in ACC2 (AJ575592), respectively. Based upon the computational prediction of a novel ACC2 splice isoform, the ACC2 exon IA and exon 5 primer set (hereafter ACC2,A-5 primer set) was expected to amplify a 472 base pair amplicon representing the ACC2 mRNA region of the predicted alternatively spliced isoform. The ACC2 exon 1A forward primer has the sequence: 5' CAAGTGCAAGATCTGTTTCCCTGATCG 3' (SEQ ID NO 7); and the ACC2 exon 5 reverse primer has the sequence: 5' CCGGAAGTTTAGGGTTTTCTGAAGCAT 3' (SEQ ID NO 8).

Twenty-five ng of polyA mRNA from adipose tissue, skeletal muscle, heart, liver, and testis was subjected to a one-step reverse transcription-PCR amplification protocol using the Qiagen, Inc. (Valencia, Calif.), One-Step RT-PCR kit, using the following cycling conditions:

50° C. for 30 minutes;
95° C. for 15 minutes;
35 cycles of:
 94° C. for 30 seconds;
 63.5° C. for 40 seconds;
 72° C. for 50 seconds; then
 72° C. for 10 minutes.

RT-PCR amplification products (amplicons) were size fractionated on a 2% agarose gel. Selected amplicon fragments were manually extracted from the gel and purified with a Qiagen Gel Extraction Kit. Purified amplicon fragments were cloned into an Invitrogen pCR2.1 vector using the reagents and instructions provided with the TOPO TA cloning kit (Invitrogen, Carlsbad, Calif.). Clones were then sequenced from each end (using the same primers used for RT-PCR) by Qiagen Genomics, Inc. (Bothell, Wash.).

The RT-PCR amplicons obtained from human adipose tissue, skeletal muscle, heart, liver, and testis polyA mRNA samples using the $ACC2_{1A-5}$ primer set exhibited the expected amplicon size of 472 base pairs for alternatively spliced ACC2 mRNA (data not shown).

Sequence analysis of the about 472 base pair amplicon revealed that this amplicon form results from the deletion of exon 1 of the ACC2 heteronuclear RNA (hnRNA) and the retention of sequence from intron 1, forming a novel 5' exon, referred to as exon 1A. This splice variant form was designated ACC2sv1 (SEQ ID NO 3). Thus, the RT-PCR results suggested that ACC2 mRNA in some tissue samples is composed of a mixed population of molecules wherein in at least one of the ACC2 mRNA splice junctions is altered.

Example 2

Cloning of ACC2sv1

Computational prediction, RT-PCR, and sequencing data indicate that in addition to the normal ACC2 reference mRNA sequence, AJ575592, encoding ACC2 protein, CAE01471, a novel splice variant form of ACC2 mRNA also exists in adipose tissue, skeletal muscle, heart, liver, and testis.

Method 1

Clones having a nucleotide sequence comprising the splice variant identified in Example 1 (hereafter referred to as ACC2sv1) are isolated using a 5' "forward" ACC2sv1 primer and a 3' "reverse" ACC2sv1 primer, to amplify and clone the entire ACC2sv1 mRNA coding sequences. The 5' "forward" primer is designed for isolation of full length clones corresponding to the ACC2sv1 splice variant and has the nucleotide sequence of 5' GAGCCCGGTGGGATT GGCCTGCGGGGTGGTCAACATGAGT 3' (SEQ ID NO 9). The 3' "reverse" primer is designed for isolation of full length clones corresponding to the ACC2sv1 splice variant and has the nucleotide sequence of 5' TCAGGTGGAGGC-CGGGCTGTCCATGGTAGACAG 3' (SEQ ID NO 10).

RT-PCR

The ACC2sv1 cDNA sequence is cloned using a combination of reverse transcription (RT) and polymerase chain reaction (PCR), using the Titan One Tube RT-PCR Kit (Roche Applied Science, Indianapolis, Ind.). More specifically, about 25 ng of adipose tissue polyA mRNA (BD Biosciences Clontech, Palo Alto, Calif.) is reverse transcribed using AMV Reverse Transcriptase and amplified using the Expand High Fidelity enzyme mixture in a one step reaction system according to the Titan One Tube RT-PCR Kit manufacturer's instructions. Reactions components are set up as two separate Master Mixes. Master Mix 1 contains the following components final concentrations in a 25 μl total reaction volume: 0.2 mM dNTPs (each), 5 mM DTT solution, 5 U RNase Inhibitor, 0.4 μM ACC2sv1 "forward" primer (SEQ ID NO 9), 0.4 μM ACC2sv1 "reverse" primer (SEQ ID NO 10), 25 ng adipose tissue RNA, and sterile water to 25 μl final volume. Master Mix 2 contains the following components in a 25 μl total reaction volume: 14 μl sterile water, 10 μl 5× RT-PCR buffer, and 1 μl enzyme mix. 25 μl of each Master Mix 1 and 2 are combined and placed on ice. For the RT step, the sample is placed in a thermocycler for 30 minutes at 48° C. The RT step is followed by a thermocycling step, which is done in a Gene Amp PCR System 9700 (Applied Biosystems, Foster City, Calif.). After an initial 94° C. denaturation of 2 minutes, 10 cycles of amplification are performed using a 30 second denaturation at 94° C. followed by a 30 second annealing at 63.5° C., and a 5 minute synthesis at 68° C. The 10 cycles of PCR are followed by an additional 25 cycles of a 30 second denaturation at 94° C., followed by a 30 second annealing at 63.5° C., and a 5 minute synthesis at 68° C. +cycle elongation of 5 seconds for each successive cycle (i.e., cycle 11 has an additional 5 seconds, cycle 12 has an additional 10 seconds). The additional 15 cycles are followed by a 7 minute extension at 68° C. The 50 μl reaction is then chilled to 4° C. 10 μl of the resulting reaction product is run on a 1% agarose (Invitrogen, Ultra pure) gel stained with 0.3 μg/ml ethidium bromide (Fisher Biotech, Fair Lawn, N.J.). Nucleic acid bands in the gel are visualized and photographed on a UV light box to determine if the PCR had yielded products of the expected size, in the case of the predicted ACC2sv1 mRNA, a product of about 6811 base pairs. The remainder of the 50 μl PCR reactions from adipose tissue is purified using the QIAquik Gel extraction Kit (Qiagen, Valencia, Calif.) following the QIAquik PCR Purification Protocol provided with the kit. About 50 μl of product obtained from the purification protocol is concentrated to about 6 μl by drying in a Speed Vac Plus (SC110A, from Savant, Holbrook, N.Y.) attached to a Universal Vacuum System 400 (also from Savant) for about 30 minutes on medium heat.

Cloning of RT-PCR Products

About 4 µl of the 6 µl of purified ACC2sv1 RT-PCR product from adipose tissue are used in a cloning reaction using the reagents and instructions provided with the pCR8/GW/TOPO TA cloning kit (Invitrogen, Carlsbad, Calif.). About 2 µl of the cloning reaction is used following the manufacturer's instructions to transform TOP10 chemically competent E. coli provided with the cloning kit. After the 1 hour recovery of the cells in SOC medium (provided with the TOPO TA cloning kit), 200 µl of the mixture is plated on LB medium plates (Sambrook, et al., in *Molecular Cloning, A Laboratory Manual*, 2$^{nd}$ Edition, Cold Spring Harbor Laboratory Press, 1989) containing 100 µg/ml Spectinomycin (Sigma, St. Louis, Mo.). Plates are incubated overnight at 37° C. Colonies are picked from the plates into 2 ml of 2× LB medium. These liquid cultures are incubated overnight on a roller at 37° C. Plasmid DNA is extracted from these cultures using the Qiagen (Valencia, Calif.) Qiaquik Spin Miniprep kit.

Twelve putative ACC2sv1 clones are identified and prepared for a PCR reaction to confirm the presence of the expected ACC2sv1 structure. A 25 µl PCR reaction is performed using the Expand High Fidelity PCR System (Roche Applied Science, Indianapolis, Ind.) following manufacturer's instructions to detect the presence of ACC2sv1, except that the reaction includes miniprep DNA from the TOPO TA/ACC2sv1 cloning reaction as a template. About 10 µl of each 25 µl PCR reaction are run on a 1% agarose gel and the DNA bands generated by the PCR reaction are visualized and photographed on a UV light box to determine which minipreps samples have PCR product of the size predicted for the corresponding ACC2sv1 mRNA. Clones having the ACC2sv1 structure are identified based upon amplification of an amplicon band of 6811 base pairs. DNA sequence analysis of the ACC2sv1 cloned DNA confirms a polynucleotide sequence representing the deletion of exon 1 and presence of exon 1A.

The polynucleotide sequence of ACC2sv1 mRNA (SEQ ID NO 3) lacks a 653 base pair region corresponding to exon 1 of the full length coding sequence of the reference ACC2 mRNA (AJ575592) and retains a 261 base pair region deriving from the sequence of intron 1, also known as exon 1A. Conceptual translation of the ACC2sv1 mRNA suggests the presence of an alternative start codon in exon 1A, located 47 nucleotides from the end of exon 1A. The replacement of exon 1 with exon 1A and the use of alternative start codon in exon 1A do not alter the protein translation reading frame. Therefore, the ACC2sv1 polypeptide possesses a unique N-terminal 16 amino acid region corresponding to exon IA and is lacking an N-terminal 218 amino acid region corresponding to exon 1 of the full length coding sequence of the reference ACC2 mRNA (AJ575592). The unique N-terminal mitochondrial localization sequence is missing in ACC2sv1, which is most likely localized in the cytoplasm and may have an alternative function to regulation of mitochondrial fatty acid oxidation, such as fatty acid synthesis (Ha et al., 1996, Proc. Natl. Acad. Sci. USA 93:11466–11470; Abu-Elheiga et al., 2000, Proc. Natl. Acad. Sci. USA 97:1444–1449).

Method 2

Cloning of ACC2sv1

The ACC2sv1 cDNA sequence was cloned by amplifying a partial fragment of ACC2sv1 cDNA encompassing exon 1A, which is unique to ACC2sv1, and exon 2 using a 5' "forward" ACC2sv1 exon 1A primer and a 3' "reverse" ACC2sv1 exon 2 primer. The 5' "forward" ACC2sv1 exon 1A primer has the nucleotide sequence of 5' <u>GCCTAGGTA</u>ATGAGTCCTGCCAAGTGCAAGATCT GTTTCCCTGATCGCGAAGTAA AGCCGAGCAT-GTCGGGACTCCA 3' (SEQ ID NO 11). The 3' "reverse" ACC2sv1 exon 2 primer has the nucleotide sequence of 5' GGCCGGTGCTTCCTCAAC 3' (SEQ ID NO 12). Specific restriction site added to the 5' "forward" ACC2sv1 exon 1A primer (SEQ ID NO 11) is represented by the underlined text. PCR was performed using the full length ACC2 reference cDNA clone as template and KOD-plus-DNA polymerase (TOYOBO, Osaka, Japan). After an initial denaturation at 94° C. for 2 minutes, 20 cycles of amplification were performed using a second denaturation at 94° C., followed by a 30 second annealing at 55° C., and a 2 minute extension at 68° C. The PCR product was then digested with AvrII and HindIII restriction enzymes and then run on a 1% agarose gel. A PCR product of the expected size, approximately 760 base pairs, was extracted and purified by QIAquick Gel Extraction Kit (Qiagen, Hilden, Germany). The purified amplicon was then ligated to an ACC2 reference cDNA clone which lacks exons 1 and 2 using the Ligation High reagent (TOYOBO, Osaka, Japan) to yield a full-length ACC2sv1 clone.

Cloning of Full-Length ACC2

Clones having the human ACC2 reference sequence which contain the mitochondrial localization sequence were isolated by PCR using human skeletal muscle Marathon-Ready cDNA as template (BD Biosciences, Palo Alto, Calif.) and LA Taq polymerase (TAKARA BIO Inc. Shiga, Japan). A 5' "forward" ACC2 primer and a 3' "reverse" ACC2 primer were designed to amplify and clone the entire ACC2 mRNA coding sequences. The 5' "forward" ACC2 primer has the nucleotide sequence of 5' <u>GCCTAGGTA</u>ATGGTCTTGCTTCTTTGTCTATCTTGT CTG 3' (SEQ ID NO 13). The 3' "reverse" ACC2 primer has the nucleotide sequence of 5' <u>ACCGGT</u>GGTGGAGGCCGGGCTGTCCATG 3' (SEQ ID NO 14). Specific restriction sites added to the 5' "forward" ACC2 primer (SEQ ID NO 13) and the 3' "reverse ACC2 primer (SEQ ID NO 14) are represented by the underlined text. Thirty cycles of amplification were performed in a Gene Amp PCR System 9700 (Applied Biosystems, Foster City, Calif.) using a 10 second denaturation at 98° C., followed by a 10 minute annealing and extension step at 63° C. The resulting PCR product is run on a 0.8% agarose gel and stained with ethidium bromide. A PCR product of the expected size, approximately 7.5 kb in the case of ACC2, was extracted and purified by QIAquick Gel Extraction Kit (Qiagen, Hilden, Germany). The purified ACC2 amplicon was subsequently cloned into pcDNA™5/FRTNV5-His TOPO vector (Invitrogen, Carlsbad, Calif.) using the reagents and instructions provided by the manufacturer.

Cloning of Full-Length ACC1

Clones having the human ACC1 reference sequence (NM_98834) were cloned by amplification of two separate cDNA fragments using human adipocyte Marathon-Ready cDNA (BD Biosciences, Palo Alto, Calif.) as template and the KOD-plus-DNA-polymerase (TOYOBO, Osaka, Japan). A 5' "forward" ACC1 primer and a 3' "reverse" ACC1 primer were designed to amplify an approximately 4.5 kb N-terminal fragment of ACC1. The 5' "forward" ACC1 primer has the nucleotide sequence of 5' <u>GCCTAGGATA</u>ATGGATGAACCATCTCCCTTGGCCC AACCTC 3' (SEQ ID NO 15). The 3' "reverse" ACC1 primer has the nucleotide sequence of 5' AGGACGCG-CAATTTCCACAGGCGACTTCCATACC 3' (SEQ ID NO 16). A second 5' "forward" ACC1 primer and a second 3' "reverse" ACC1 primer were designed to amplify an approximately 3.3 kb C-terminal fragment of ACC1. The second 5' forward ACC1 primer has the nucleotide sequence of 5' GAGTCCCACATTCCCTGAGGCAGGTCACACG 3' (SEQ ID NO 17). The second 3' "reverse" ACC1 primer has the nucleotide sequence of 5' ACCGGTCGTGGAAGGGGAATCCATTGTGGA 3' (SEQ ID NO 18). Specific restriction sites added to the primer sequences are indicated by the underlined text. PCR was performed in the Gene Amp PCR System 9700 (Applied Biosystems, Foster City, Calif.). After an initial denaturation at 94° C. for 2 minutes, 35 cycles of amplification were performed using a 15 second denaturation at 94° C., followed by a 30 second annealing at 55° C., and an 8 minute extension step at 68° C. The PCR products were run on a 0.5% agarose gel and the fragments corresponding to the expected sizes, 4.5 kb for the amplicon using the first set of ACC1 primers (SEQ ID NOs 15, 16) and 3.3 kb for the amplicon using the second set of ACC1 primers (SEQ ID NO 17, 18), were extracted and purified by Qiaquick Gel Extraction Kit (Qiagen, Hilden, Germany). The purified amplicons were cloned into pcDNA™5/FRTNV5-His TOPO vector (Invitrogen, Carlsbad, Calif.) using the reagents and instructions provided by the manufacturer.

To construct the full-length ACC1 coding sequence, the purified N-terminal 4.5 kb and C-terminal 3.3 kb amplicons were joined. The 4.5 kb N-terminal ACC1 clone was digested with restriction enzymes NruI and NarI. The 3.3 kb C-terminal ACC1 clone was digested with restriction enzymes NruI and NarI. The N-terminal and C-terminal ACC1 fragments were then ligated using the Takara DNA Ligation Kit (Takara Bio, Shiga, Japan) to produce a full length ACC1 cDNA clone.

Example 3

Real-time Quantitative PCR/TAQman

To determine the relative mRNA abundances of ACC2sv1 alternatively spliced isoform to the ACC2 reference transcript (AJ575592), a real-time quantitative PCR assay was used. Materials and methods for quantification of splice variants using real-time PCR, using boundary specific probes are known in the art (Kafert et al., 1999 Anal. Biochem. 269:210–213; Vandenbroucke et al, 2001 Nucleic Acids Res. 29:E68–8; Taveau et al., 2002 Anal. Biochem. 305:227–235).

Reverse Transcription

RNA samples from human heart, liver, adipose tissue, skeletal muscle, and testis (ClonTech, Palo Alto, Calif.) were reverse transcribed using the Applied Biosystems (Foster City, Calif.) TAQman reverse transcription kit N808–0234 following manufacturer's instructions. A 50 µl reaction contained:

| 5 | µl 10× RT buffer |
| 11 | µl MgCl$_2$ solution |
| 10 | µl dNTP solution |
| 2.5 | µl random hexamer primer |
| 1 | µl RNAse OUT |
| 3 | µl Multiscribe reverse transcriptase |

-continued

| 1 | µg of RNA |
| | H$_2$O to a final volume of 50 µl. |

To convert RNA to single-stranded cDNA, the reaction mixture was incubated at the following conditions: 25° C. for 10 minutes, 37° C. for 60 minutes, 95° C. for 5 minutes cDNA sample was then placed on ice prior to use.

Plasmid Construction and Standard Curve

Plasmids carrying the reference ACC2 sequence and alternatively spliced isoform ACC2sv1 were constructed in order to prepare a standard curve. The ACC2sv1 cDNA region spanning nucleotides from exon IA to exon 5 was amplified with exon 1A primer 5' CAAGTGC AAGATCT-GTTTCCCTGATCG 3' (SEQ ID NO 7) and exon 5 primer 5' CCGGAAGTTTAGG GTTTTCTGAAGCAT 3' (SEQ ID NO 8) from adipose tissue cDNA. The reference ACC2 cDNA region spanning nucleotides from exon 1 to exon 5 was amplified with exon 1 primer 5' TTATCTGACCACAG-GTGAAGCTGAGA 3' (SEQ ID NO 19) and another exon 5 primer 5' GCTCCGGAAGTTTAGGGTTTTCTAAAG 3' (SEQ ID NO 20) from adipose tissue cDNA. The PCR products were cloned into pCR2.1 vector (Invitrogen). The cloning reaction was used to transform TOP 10 chemically competent E. coli cells, and plasmid DNA was extracted using the Qiagen (Valencia, Calif.) Qiaquick Spin Miniprep kit. DNA was quantified using a UV spectrometer. Sequence identities of plasmid clones containing the ACC2 reference sequence and alternatively spliced ACC2sv1 sequence, which lacks exon 1 and contains exon 1A, were verified.

To construct a standard curve with the plasmid clones carrying the ACC2 reference sequence and ACC2sv1 sequence, ten-fold serial dilutions of the plasmids were used to obtain a range of five orders of magnitude. Final plasmid concentrations of 100 pg, 10 pg, 1 pg, 0.1 pg, and 0.01 pg were amplified using real-time PCR. Fluorescence emission values were plotted onto a standard curve, permitting quantification of the experimental samples compared to the standard curve.

Real-time PCR

TAQman primers and probes used to quantify the ACC2sv1 isoform were designed and synthesized as pre-set mixtures (Applied Biosystems, Foster City, Calif.). The sequences of the TAQman primers and probes used to quantify the ACC2 reference form (SEQ ID NOs 21, 22 and 23) and ACC2sv1 isoform (SEQ ID NOs 24, 25 and 26) are shown in Table 1. Splice junction specific probes were labeled with the 6-FAM fluorphore at the 5' end (FAM) and a non-fluorescent quencher at the 3' end (NFQ). Real-time PCR was performed on human adipose tissue, heart, liver, skeletal muscle, and testis cDNA using the TaqMan Universal PCR Master Mix (Applied Biosystems, Foster City, Calif.). The TAQman reaction contained:

| 96-well format | 384-well format | |
| --- | --- | --- |
| 12.5 µl | 5 µl | TAQman Universal MasterMix |
| 1.25 µl | 0.5 µl | Primer-probe mix |
| 6.25 µl | 2.5 µl | H$_2$O |
| 5 µl | 2 µl | cDNA or plasmid DNA. |

TABLE 1

Primers and probes used to amplify ACC2 isoforms.

| Name | SEQ ID NO | Sequence | Specificity |
|---|---|---|---|
| ACC2 reference forward primer | SEQ ID NO 21 | GACCACAGGTGAAGCTGAGA | ACC2 reference |
| ACC2 reference reverse primer | SEQ ID NO 22 | GTGTTCCCGTCCCCTCTTC | ACC2 reference |
| ACC2 reference probe | SEQ ID NO 23 | FAM-ACATGCTCGGCCTCATAG-NFQ | ACC2 reference |
| ACC2sv1 forward primer | SEQ ID NO 24 | AAGTGCAAGATCTGTTTCCCTGAT | ACC2sv1 |
| ACC2sv1 reverse primer | SEQ ID NO 25 | CAGGTGGAGTCCCGACATG | ACC2sv1 |
| ACC2sv1 probe | SEQ ID NO 26 | FAM-CTCGGCTTTACTTCGCG-NFQ | ACC2sv1 |

The TAQman reactions were performed on an ABI Prism 7900HT Sequence Detection System (Applied Biosystems, Foster City, Calif.). The thermocycling conditions were 50° C. for 2 minutes, 95° C. for 10 minutes, and 40 cycles of 95° C. for 15 seconds and 60° C. for 1 minute. Data analysis of the fluorescence emission was performed by the Sequence Detector Software (SDS) (Applied Biosystems, Foster City, Calif.). Briefly, an amplification plot was generated for each sample, which showed cycle number on the x axis vs. $\Delta R_n$ on the y axis. $R_n$ is the fluorescence emission intensity of the reporter dye normalized to a passive reference, and $\Delta R_n$ is the $R_n$ value of the reaction minus the $R_n$ of an un-reacted sample. A threshold cycle ($C_T$) value, the cycle at which a statistically significant increase in $\Delta R_n$ is first detected, was calculated from the amplification plot. The threshold was automatically calculated by the SDS as the 10-fold standard deviation of the $R_n$ in the first 15 cycles. The obtained $C_T$ values were exported Microsoft Excel for analysis as recommended by the manufacturer (Applied Biosystems, Foster City, Calif.). Standard curve plots showing the $\log_{10}$ [input cDNA] vs. $C_T$ values were constructed. Referring to the standard curve, $C_T$ values for the experimental samples were then used to calculate the input amount of the ACC2 isoform cDNA. The most highly expressed isoform, in this case the reference form of ACC2 from adipose tissue, was assigned the arbitrary value of 100%, and other isoforms from other tissues were presented as percentages the most highly expressed isoform. Quantitative analysis of the real-time PCR data indicated that the reference ACC2 is most abundant in adipose tissue compared to other human tissues: 21.4% in heart, 22.6% in liver, 87.6% in skeletal muscle, and 1.8% in testis (normalized to level of reference ACC2 in adipose tissue=100%). Quantitative analysis of the real-time PCR data indicated that the ACC2sv1 isoform was also most abundant in adipose tissue, but was less abundant than the reference ACC2 in all the tissues examined: 38.4% in adipose tissue, 7.1% in heart, 2.3% in liver, 6.3% in skeletal muscle, and 2.7% in testis (normalized to level of reference ACC2 in adipose tissue=100%). These results demonstrate that contrary to previous reports, the reference ACC2 is considerably abundant in white adipose tissue over skeletal muscle and heart, and may suggest an alternative function for ACC2, other than regulation of fatty acid oxidation in non-lipogenic tissues (Bianchi et al., 1990, J. Biol. Chem. 265:1502–1509; Ha et al., 1996, Proc. Natl. Acad. Sci. USA 93:11466–11470; Widmer et al., 1996, Biochem. J. 316: 915–922).

Example 4

Protein Expression

ACC2 and ACC2sv1 clones from cloning Method 2 of Example 2 were digested with AvrII and PmeI restriction enzymes and then subcloned into pEF cDNA expression vector (Invitrogen, Carlsbad, Calif.) which was digested by SpeI and EcoRV. The ACC2 and ACC2sv1 expression vectors were introduced into a mouse mammary carcinoma cell line FM-3A (RIKEN cell bank, #RCB0086) using the Lipofectaimine 2000 (Invitrogen, Carlsbad, Calif.) or Effectene Transfection Reagent (Qiagen, Hilden, Germany), according to manufacturer's instructions. The FM-3A cells were cultured in RPMI 1640 medium (Invitrogen, Carlsbad, Calif.) containing 10% fetal bovine serum (HiClone) and 1 mg/ml G418 (Invitrogen, Carlsbad, Calif.) at 37° C. and 5% $CO_2$ to select for transfected cells. ACC2 and ACC2sv1 protein levels were measured by Western blot analysis using HRP-conjugated streptavidin (Invitrogen, Carlsbad, Calif.).

ACC1 clone from Example 2 was digested with AvrII and PmeI restriction enzymes and then subcloned into pBac-PAK9 (BD Biosciences, Mountainview, Calif.) transfer vector, which was then digested with XbaI and StuI for generating baculovirus. The viral particles were generated in Sf9 insect cells using the reagents and instructions provided by the BacPAK Baculovirus Expression System (BD Biosciences, Mountainview, Calif.).

Preparation of Recombinant Protein

The FM-3A cells expressing ACC2 and ACC2sv1 were cultured in RPMI 1640, 10% fetal bovine serum, penicillin/streptomycin, and 0.5 mg/ml G418 at 37° C. and 5% $CO_2$.

The Sf9 cells were grown in Grace's Insect Cell Culture Medium (Invitrogen, Carlsbad, Calif.) containing 10% fetal bovine serum, 0.1 mg/ml kanamicin, and 0.1% PLU-RONIC® F-68 (Invitrogen, Carlsbad, Calif.) at 30° C. and 5% $CO_2$. Sf9 cells were collected by centrifugation and resuspended in the culture media at a cell density of $1 \times 10^7$ cells/ml. The Sf9 cells were then incubated with the virus stock solution (moi=approximately 5) for 1 hour at room temperature. The infected Sf9 cells were diluted with the culture media to cell density of $1 \times 10^6$ cells, and then cultured for 3 days.

The following protein extraction and purification procedures were performed at 4° C. unless noted. The cell suspensions were collected by centrifugation and the cell pellets were resuspended in 5× volume of lysis buffer (50 mM Tris-HCl (pH 7.5), 0.5 M NaCl, 5% glycerol, 12 mM imidazole, complete-EDTA protease inhibitor cocktail (Roche Diagnostics, Basel, Switzerland). Then the cells were homogenized with a Polytron homogenizer, followed by a Potter homogenizer. The cell lysate was centrifuged at 20,000×g for 30 minutes, and the supernatant was re-centrifuged at 38,000 rpm in a RP45T rotor (Hitachi Koki Co., Tokyo, Japan) for 60 minutes. The resulting supernatant was applied to a Ni-charged HiTrp chelating column (Amersham Biosciences, Pisxataway, N.J.). The Ni column was then washed with 10× volume of 50 mM Tris-HCl buffer (pH 7.5) containing 0.5 M NaCl and 5% glycerol. The remaining proteins were eluted from the column by imidazole at 0–500 mM, and the elution fractions were monitored by spectrophotometry at 280 nm. ACC1, ACC2, and ACC2sv1 protein and activity in each fraction were measured.

Example 5

ACC Activity Assay

ACC1, ACC2, and ACC2sv1 activity were measured by a standard $^{14}CO_2$ fixation assay that measures the incorporation of [$^{14}C$]bicarbonate into [$^{14}C$]malonyl-CoA, and separates the product from unused substrate at the end of the reaction through acidification, which serves to both quench the reaction and remove residual radiolabeled substrate as $^{14}CO_2$. The standard $^{14}CO_2$ fixation assay is known in the art and has also been described in US 2003/0144345, Witters et al. (1988, Proc. Natl. Acad. Sci. USA 85:5473–5477), Bianchi et al. (1990, J. Biol. Chem. 265:1502–1509), and Winder et al. (1997, J. Appl. Physiol. 82:219–225). Briefly, protein samples were incubated at 37° C. for 40 minutes in a reaction mixture consisting of 50 mM HEPES (pH 7.5), 2 mM DTT, 20 mM $MgCl_2$, 20 mM citrate, 4 mM acetyl-CoA, 5 mM ATP, 4 mM $NaHCO_3$, and 0.08 mM [$^{14}C$]$NaHCO_3$ (50–62 mCi/mmol, Amersham Biosciences), and the reaction was terminated with 1 N HCl. Following evaporation of reaction liquids, Microscint™ 40 liquid scintillation cocktail (Perkin Elmer, Boston, Mass.) was added to the remaining mixture containing the $^{14}C$-labeled malonyl-CoA reaction product. Radioactivity was measured by a TopCount liquid scintillation counter (Perkin Elmer, Boston, Mass.). Table 2 presents the enzyme kinetics of ACC1, ACC2, and ACC2sv1 for various substrates.

TABLE 2

| Enzyme kinetic characteristics ($K_m$) of ACCs against various substrates | | | |
|---|---|---|---|
| Substrate | ACC1 | ACC2 | ACC2sv1 |
| Acetyl-CoA (μM) | 51 | 108 | 94 |
| ATP (μM) | 54 | 44 | 109 |
| $HCO_3$ (mM) | 6.47 | 2.89 | 6.51 |

All patents, patent publications, and other published references mentioned herein are hereby incorporated by reference in their entireties as if each had been individually and specifically incorporated by reference herein. While preferred illustrative embodiments of the present invention are shown and described, one skilled in the art will appreciate that the present invention can be practiced by other than the described embodiments, which are presented for purposes of illustration only and not by way of limitation. Various modifications may be made to the embodiments described herein without departing from the spirit and scope of the present invention. The present invention is limited only by the claims that follow.

What is claimed is:

1. A method of screening for a compound that modulates activity of acetyl coenzyme A carboxylase 2, splice variant 1 (ACC2sv1) comprising:
   (a) expressing a recombinant nucleic acid encoding ACC2sv1 comprising SEQ ID NO 4 in a cell;
   (b) contacting said cell or a cell extract thereof with a test preparation comprising one or more test compounds; and
   (c) measuring the effect of said test preparation on enzyme activity.

2. The method of claim 1, wherein said recombinant nucleic acid encoding ACC2sv1 also comprises an expression vector.

3. The method of claim 1, wherein said test preparation contains a compound that is an ACC inhibitor.

4. The method of claim 1, wherein said cell expressing a recombinant nucleic acid encoding ACC2sv1 comprising SEQ ID NO 4 is homogenized to obtain a cell extract and step (b) is performed by contacting said cell extract with said test preparation.

5. The method of claim 1, wherein said enzyme activity is measured using a $CO_2$ fixation assay.

6. The method of claim 1 wherein said measuring is performed using a high throughput format.

7. The method of claim 1 wherein, said test preparation comprises one or more agonists, antagonists, or allosteric modulators of ACC2sv1.

8. The method of claim 4 additionally comprising comparing said measured level of ACC2sv1 activity to the level of acetyl coenzyme A carboxylase activity in a control cell not expressing a recombinant nucleic acid encoding ACC2sv1.

9. The method of claim 4 additionally comprising comparing said measured level of ACC2sv1 activity to the level of acetyl coenzyme A carboxylase (ACC) activity in a cell expressing a recombinant nucleic acid encoding an ACC isofform polypeptide that is not ACC2sv1.

* * * * *